US012661409B2

(12) United States Patent
Disney

(10) Patent No.: US 12,661,409 B2
(45) Date of Patent: Jun. 23, 2026

(54) TARGET VALIDATION AND PROFILING OF THE RNA TARGETS OF SMALL MOLECULES

(71) Applicant: University of Florida Research Foundation, Incorporated, Gainesville, FL (US)

(72) Inventor: Matthew D. Disney, Jupiter, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1241 days.

(21) Appl. No.: 17/284,297

(22) PCT Filed: Sep. 26, 2019

(86) PCT No.: PCT/US2019/053179

§ 371 (c)(1),
(2) Date: Apr. 9, 2021

(87) PCT Pub. No.: WO2020/076511

PCT Pub. Date: Apr. 16, 2020

(65) Prior Publication Data

US 2021/0379188 A1 Dec. 9, 2021

Related U.S. Application Data

(60) Provisional application No. 62/743,996, filed on Oct. 10, 2018.

(51) Int. Cl.

| | |
|---|---|
| ***A61K 47/55*** | (2017.01) |
| ***A61K 31/704*** | (2006.01) |
| ***C12N 15/11*** | (2006.01) |

(52) U.S. Cl.

CPC ............ *A61K 47/55* (2017.08); *A61K 31/704* (2013.01); *C12N 15/111* (2013.01); *C12N 2310/141* (2013.01); *C12N 2320/10* (2013.01)

(58) Field of Classification Search

CPC ...... A61K 31/704; A61K 47/54; A61K 47/55; C12N 15/111; C12N 2310/141; C12N 2320/10

See application file for complete search history.

(56) References Cited

U.S. PATENT DOCUMENTS

| | | | | |
|---|---|---|---|---|
| 8,071,562 | B2 | 12/2011 | Bader et al. | |
| 9,586,944 | B2 | 3/2017 | Disney et al. | |
| 9,933,419 | B2 | 4/2018 | Disney et al. | |
| 10,157,261 | B2 | 12/2018 | Disney et al. | |
| 11,636,918 | B2 | 4/2023 | Disney et al. | |
| 2008/0188377 | A1 * | 8/2008 | Disney ................. | C12Q 1/6811 506/9 |
| 2008/0227213 | A1 | 9/2008 | Disney | |
| 2010/0190826 | A1 | 7/2010 | Kakefuda et al. | |
| 2012/0277178 | A1 | 11/2012 | Jin et al. | |
| 2014/0212945 | A1 | 7/2014 | Disney | |
| 2016/0188791 | A1 | 6/2016 | Disney | |
| 2016/0194696 | A1 | 7/2016 | Guan et al. | |
| 2017/0029370 | A1 | 2/2017 | Narayanan et al. | |
| 2017/0362650 | A1 | 12/2017 | Zeitlinger et al. | |
| 2018/0066262 | A1 | 3/2018 | Domenyuk et al. | |
| 2018/0267028 | A1 | 9/2018 | Disney et al. | |
| 2019/0156912 | A1 | 5/2019 | Disney et al. | |
| 2019/0270723 | A1 | 9/2019 | Kumaravel et al. | |
| 2020/0115372 | A1 | 4/2020 | Petter et al. | |
| 2020/0324287 | A1 | 10/2020 | Vijayan et al. | |
| 2020/0385709 | A1 | 12/2020 | Wagner | |
| 2021/0008208 | A1 | 1/2021 | Poma et al. | |
| 2022/0073910 | A1 | 3/2022 | Disney | |
| 2022/0119868 | A1 | 4/2022 | Disney | |
| 2022/0251545 | A1 | 8/2022 | Disney | |

(Continued)

FOREIGN PATENT DOCUMENTS

| | | | |
|---|---|---|---|
| CN | 110494443 | A | 11/2019 |
| WO | WO 2005/068433 | A1 | 7/2005 |

(Continued)

OTHER PUBLICATIONS

Rzuczek et al.(Nat. Chem. Biol., 2017, 13:188-193) (Year: 2017).*
Disney et al. (Acc. Chem. Res., 2016, 49:2698-2704) (Year: 2016).*
Guan et al. (Angew. Chem. Int. Ed., 2013, 52:1462-1465) (Year: 2013).*
Velagapudi et al. (Proc. Natl. Acad. Sci., 2016, 113(21):5898-5903) (Year: 2016).*
"An integrated encyclopedia of DNA elements in the human genome", Nature, vol. 489, (Sep. 6, 2012), 57-74.
"International Application No. PCT/US2019/053179, International Search Report and Written Opinion mailed Feb. 28, 2020", (Feb. 28, 2020), 14 pgs.
Bevilacqua, Philip C., et al., "Genome-Wide Analysis of RNA Secondary Structure", Ann. Rev. Genet. 50, 235-266 (2016), (Sep. 14, 2016), 235-266.

(Continued)

*Primary Examiner* — Jeremy C Flinders
(74) *Attorney, Agent, or Firm* — Wolf, Greenfield & Sacks, P.C.

(57) ABSTRACT

A method for the precise cellular destruction of an oncogenic non-coding RNA with a RNA-binding small molecule conjugated with bleomycin A5 is described. The method affords reversal of phenotype. Bleomycin A5 was coupled to an RNA-binding molecule that selectively binds the microRNA-96 hairpin precursor (pri-miR-96). By coupling of bleomycin A5's free amine to the RNA-binding molecule, its affinity for binding to pri-miR-96 is >100-fold stronger than to DNA. The conjugate compound selectively cleaves pri-miR-96 in triple negative breast cancer (TNBC) cells. Selective cleavage of pri-miR-96 enhances expression of FOXO1 protein, a pro-apoptotic transcription factor that miR-96 silences, and triggers apoptosis in TNBC cells. No effects were observed in healthy breast epithelial cells. This method provides programmable control for targeting RNA through the selection of an RNA-binding molecule/bleomycin A5 conjugate and provides a facile method of mapping the cellular binding sites of an RNA-binding molecule.

33 Claims, 5 Drawing Sheets

Specification includes a Sequence Listing.

(56) References Cited

U.S. PATENT DOCUMENTS

2022/0267839 A1 8/2022 Disney
2023/0002329 A1 1/2023 Disney et al.
2023/0041228 A1 2/2023 Disney
2023/0149554 A1 5/2023 Disney
2024/0293398 A1 9/2024 Disney et al.
2025/0051762 A1 2/2025 Disney et al.

FOREIGN PATENT DOCUMENTS

WO WO 2006/133022 A2 12/2006
WO WO 2007/127212 A2 11/2007
WO WO 2008/066873 A2 6/2008
WO WO 2008/103489 A2 8/2008
WO WO 2009/036000 A2 3/2009
WO WO 2011/150494 A1 12/2011
WO WO 2013/019469 A1 2/2013
WO WO 2015/009678 A2 1/2015
WO WO 2015/021415 A1 2/2015
WO WO 2016/085659 A1 6/2016
WO WO 2016/191604 A1 12/2016
WO WO 2017/196264 A1 11/2017
WO WO 2018/006074 A2 1/2018
WO WO-2018098297 A1 5/2018
WO WO 2018/151810 A1 8/2018
WO WO 2019/109046 A1 6/2019
WO WO 2019/209975 A1 10/2019
WO WO 2019/231821 A1 12/2019
WO WO-2020076511 A1 4/2020
WO WO 2021/087084 A1 5/2021

OTHER PUBLICATIONS

Howe, John, et al., "Selective small-molecule inhibition of an RNA structural element", Nature, vol. 526, (Oct. 29, 2015), 672-677.
Lu, Zhipeng, et al., "Decoding the RNA structurome", Curr Opin Struct Biol. Feb. 2016; 36: 142-148, (Feb. 2016), 142-148.
Naryshkin, Nikolai A., et al., "SMN2 splicing modifiers improve motor function and longevity in mice with spinal muscular atrophy", Science 345 (6197), 688-693 (2014), (Aug. 4, 2014), 688-693.
Palacino, James, et al., "SMN2 splice modulators enhance U1-pre-mRNA association and rescue SMA mice", Nature Chemical Biology, vol. 11, 511-517 (2015), (Jun. 1, 2015), 511-517.
Ratmeyer, Lynda S., et al., "An ethidium analog that binds with high specificity to a base-bulged duplex from the TAR RNA region of the HIV-1 genome", J. Med. Chem. 1992, 35, 5, 966-968, (Mar. 1, 1992), 966-968.
Tenson, Tanel, et al., "Antibiotics and the ribosome", Molecular Microbiology (2006) 59(6), 1664-1677, (Jan. 30, 2006), 1664-1677.
Velagapudi, Sai Pradeep, et al., "Design of a small molecule against an oncogenic noncoding RNA", PNAS, vol. 113, No. 21, (May 24, 2016), 5898-5903.
[No Author Listed], CAS Registry No. 1045308-20-0. Entered Aug. 31, 2008. Chemical Abstracts Service, Columbus, OH.
Abraham et al., RNA cleavage and inhibition of protein synthesis by bleomycin. Chem Biol. Jan. 2003;10(1):45-52. doi: 10.1016/s1074-5521(02)00306-x.
Agarwal et al., Predicting effective microRNA target sites in mammalian mRNAs. Elife. Aug. 12, 2015;4:e05005. doi: 10.7554/eLife.05005.
Angelbello et al., Bleomycin Can Cleave an Oncogenic Noncoding RNA. Chembiochem. Jan. 4, 2018;19(1):43-47. doi: 10.1002/cbic.201700581. Epub Nov. 22, 2017. Author manuscript, 10 pages.
Benhamou et al., DNA-encoded library versus RNA-encoded library selection enables design of an oncogenic noncoding RNA inhibitor. Proc Natl Acad Sci U S A. Feb. 8, 2022;119(6):e2114971119. doi: 10.1073/pnas.2114971119. Supporting Information included. 80 pages total.
Berger et al., Activity-based protein profiling: applications to biomarker discovery, in vivo imaging and drug discovery. Am J Pharmacogenomics. 2004;4(6):371-81. doi: 10.2165/00129785-200404060-00004.
Berry et al., DNA damage and growth inhibition in cultured human cells by bleomycin congeners. Biochemistry. Jun. 18, 1985;24(13):3207-14. doi: 10.1021/bi00334a020.
Boger et al., Definition of the Effect and Role of the Bleomycin A2 Valerate Substituents: Preorganization of a Rigid, Compact Conformation Implicated in Sequence-Selective DNA Cleavage. J. Am. Chem. Soc. 1998;120(36):9149-58.
Boger et al., Synthesis of key analogs of bleomycin A2 that permit a systematic evaluation of the linker region: identification of an exceptionally prominent role for the L-threonine substituent. Bioorg Med Chem. Sep. 1995;3(9):1281-95. doi: 10.1016/0968-0896(95)00113-u.
Boger et al., Total Synthesis of Bleomycin A2 and Related Agents. 1. Synthesis and DNA Binding Properties of the Extended C-Terminus: Tripeptide S, Tetrapeptide S, Pentapeptide S, and Related Agents. J. Am. Chem. Soc. Jun. 1994;116(13):5607-18.
Burger, Cleavage of Nucleic Acids by Bleomycin. Chem Rev. May 7, 1998;98(3):1153-1170. doi: 10.1021/cr960438a.
Carter et al., Site-specific cleavage of RNA by Fe(II).bleomycin. Proc Natl Acad Sci U S A. Dec. 1990;87(23):9373-7. doi: 10.1073/pnas.87.23.9373.
Childs-Disney et al., A Massively Parallel Selection of Small Molecule-RNA Motif Binding Partners Informs Design of an Antiviral from Sequence. Chem. Oct. 11, 2018;4(10):2384-2404. doi: 10.1016/j.chempr.2018.08.003. Epub Sep. 13, 2018.
Childs-Disney et al., A Small Molecule Microarray Program Platform to Select RNA Internal Loop-Ligand Interactions. ACS Chem Biol. Nov. 20, 2007;2(11):745-54. doi: 10.1021/cb700174r. Epub Nov. 2, 2007.
Childs-Disney et al., Approaches to Validate and Manipulate RNA Targets with Small Molecules in Cells. Annu Rev Pharmacol Toxicol. 2016;56:123-40. doi: 10.1146/annurev-pharmtox-010715-103910. Epub Oct. 22, 2015.
Childs-Disney et al., Induction and reversal of myotonic dystrophy type 1 pre-mRNA splicing defects by small molecules. Nat Commun. 2013;4:2044. doi: 10.1038/ncomms3044. Author manuscript, 28 pages.
Childs-Disney et al., Rationally designed small molecules targeting the RNA that causes myotonic dystrophy type 1 are potently bioactive. ACS Chem Biol. May 18, 2012;7(5):856-62. doi: 10.1021/cb200408a. Epub Mar. 5, 2012. Author manuscript, 16 pages.
Childs-Disney et al., Using modularly assembled ligands to bind RNA internal loops separated by different distances. Chembiochem. Sep. 19, 2011;12(14):2143-6. doi: 10.1002/cbic.201100298. Epub Aug. 9, 2011. Author manuscript, 9 pages.
Costales et al., A Designed Small Molecule Inhibitor of a Non-Coding RNA Sensitizes HER2 Negative Cancers to Herceptin. J Am Chem Soc. Feb. 20, 2019;141(7):2960-2974. doi: 10.1021/jacs.8b10558. Epub Feb. 6, 2019.
Costales et al., Small Molecule Inhibition of microRNA-210 Reprograms an Oncogenic Hypoxic Circuit. J Am Chem Soc. Mar. 8, 2017;139(9):3446-3455. doi: 10.1021/jacs.6b11273. Epub Feb. 27, 2017. Author manuscript, 24 pages.
Costales et al., Small Molecule Targeted Recruitment of a Nuclease to RNA. J Am Chem Soc. Jun. 6, 2018;140(22):6741-6744. doi: 10.1021/jacs.8b01233. Epub May 24, 2018. Author manuscript, 8 pages.
Costales et al., Small-molecule targeted recruitment of a nuclease to cleave an oncogenic RNA in a mouse model of metastatic cancer. Proc Natl Acad Sci U S A. Feb. 4, 2020;117(5):2406-2411. doi: 10.1073/pnas.1914286117. Epub Jan. 21, 2020. Correction to Supporting Information for Small-molecule targeted recruitment of a nuclease to cleave an oncogenic RNA in a mouse model of metastatic cancer. Proc Natl Acad Sci U S A. May 3, 2022;119(18):e2204149119. doi: 10.1073/pnas.2204149119. Epub Apr. 26, 2022. Supporting information included. 149 pages total.
Costales et al., Targeted Degradation of a Hypoxia-Associated Non-coding RNA Enhances the Selectivity of a Small Molecule Interacting with RNA. Cell Chem Biol. Aug. 15, 2019;26(8):1180-1186.e5. doi: 10.1016/j.chembiol.2019.04.008. Epub May 23, 2019.
Cravatt et al., Activity-based protein profiling: from enzyme chemistry to proteomic chemistry. Annu Rev Biochem. 2008;77:383-414. doi: 10.1146/annurev.biochem.75.101304.124125.

(56) References Cited

OTHER PUBLICATIONS

Disney et al., Drugging the RNA World. Cold Spring Harb Perspect Biol. Nov. 1, 2018;10(11):a034769. doi: 10.1101/cshperspect.a034769.

Disney et al., Identifying and validating small molecules interacting with RNA (SMIRNAs). Methods Enzymol. 2019:623:45-66. doi: 10.1016/bs.mie.2019.04.027. Epub May 15, 2019.

Disney et al., Inforna 2.0: A Platform for the Sequence-Based Design of Small Molecules Targeting Structured RNAs. ACS Chem Biol. Jun. 17, 2016;11(6):1720-8. doi: 10.1021/acschembio.6b00001. Epub Apr. 20, 2016. Author manuscript, 19 pages.

Disney et al., Two-Dimensional Combinational Screening Identifies Specific Aminoglycoside-RNA Internal Loop Partners. J Am Chem Soc. Aug. 20, 2008;130(33):11185-94. doi: 10.1021/ja803234t. Epub Jul. 25, 2008.

Disney, Targeting RNA with Small Molecules to Capture Opportunities at the Intersection of Chemistry, Biology, and Medicine. J Am Chem Soc. May 1, 2019;141(17):6776-6790. doi: 10.1021/jacs.8b13419. Epub Apr. 19, 2019. Author manuscript, 29 pages.

Frankel et al., Programmed cell death 4 (PDCD4) is an important functional target of the microRNA miR-21 in breast cancer cells. J Biol Chem. Jan. 11, 2008;283(2):1026-33. doi: 10.1074/jbc.M707224200. Epub Nov. 8, 2007.

Graczyk, Gini coefficient: a new way to express selectivity of kinase inhibitors against a family of kinases. J Med Chem. Nov. 15, 2007;50(23):5773-9. doi: 10.1021/jm070562u. Epub Oct. 19, 2007.

Griffiths-Jones et al., miRBase: tools for microRNA genomics. Nucleic Acids Res. Jan. 2008;36(Database issue):D154-8. doi: 10.1093/nar/gkm952. Epub Nov. 8, 2007.

Guan et al., Covalent small-molecule-RNA complex formation enables cellular profiling of small-molecule-RNA interactions. Angew Chem Int Ed Engl. Sep. 16, 2013;52(38):10010-3. doi: 10.1002/anie.201301639. Epub Aug. 1, 2013. Author manuscript, 9 pages.

Guan et al., Recent Advances in Developing Small Molecules Targeting RNA. ACS Chem Biol. Jan. 20, 2012;7(1):73-86. doi: 10.1021/cb200447r. Epub Jan. 12, 2012.

Guttilla et al., Coordinate regulation of FOXO1 by miR-27a, miR-96, and miR-182 in breast cancer cells. J Biol Chem. Aug. 28, 2009;284(35):23204-16. doi: 10.1074/jbc.M109.031427. Epub Jul. 1, 2009.

Hecht, The Chemistry of Activated Bleomycin. Acc. Chem. Res. Dec. 1986;19:383-91.

Hermann, Small molecules targeting viral RNA. Wiley Interdiscip Rev RNA. Nov. 2016;7(6):726-743. doi: 10.1002/wrna.1373. Epub Jun. 16, 2016.

Huang et al., MiR-210—micromanager of the hypoxia pathway. Trends Mol Med. May 2010;16(5):230-7. doi: 10.1016/j.molmed.2010.03.004. Epub Apr. 29, 2010. Author manuscript, 16 pages.

Iliopoulos et al., STAT3 activation of miR-21 and miR-181b-1 via PTEN and CYLD are part of the epigenetic switch linking inflammation to cancer. Mol Cell. Aug. 27, 2010;39(4):493-506. doi: 10.1016/j.molcel.2010.07.023.

Im et al., Identification of aminosulfonylarylisoxazole as microRNA-31 regulators. PLoS One. Aug. 4, 2017;12(8):e0182331. doi: 10.1371/journal.pone.0182331.

Kane et al., Polynucleotide recognition and degradation by bleomycin. Prog Nucleic Acid Res Mol Biol. 1994;49:313-52. doi: 10.1016/s0079-6603(08)60054-9.

Krichevsky et al., miR-21: a small multi-faceted RNA. J Cell Mol Med. Jan. 2009;13(1):39-53. doi: 10.1111/j.1582-4934.2008.00556.x.

Kunig et al., DNA-encoded libraries—an efficient small molecule discovery technology for the biomedical sciences. Biol Chem. Jun. 27, 2018;399(7):691-710. doi: 10.1515/hsz-2018-0119.

Kwok et al., Determination of in vivo RNA structure in low-abundance transcripts. Nat Commun. 2013;4:2971. doi: 10.1038/ncomms3971.

Lang et al., DOCK 6: combining techniques to model RNA-small molecule complexes. RNA. Jun. 2009;15(6):1219-30. doi: 10.1261/rna.1563609. Epub Apr. 15, 2009.

Lee et al., Controlling the specificity of modularly assembled small molecules for RNA via ligand module spacing: targeting the RNAs that cause myotonic muscular dystrophy. J Am Chem Soc. Dec. 2, 2009;131(47):17464-72. doi: 10.1021/ja906877y.

Li et al., Synthesis of linear polyether polyol derivatives as new materials for bioconjugation. Bioconjug Chem. Apr. 2009;20(4):780-9. doi: 10.1021/bc900036f.

Li Y et al., Precise Small Molecule Degradation of a Noncoding RNA Identifies Cellular Binding Sites and Modulates an Oncogenic Phenotype. ACS Chem Biol. Nov. 16, 2018;13(11):3065-3071. doi: 10.1021/acschembio.8b00827. Epub Oct. 30, 2018. Author Manuscript 15 pages.

Liu et al., Analysis of secondary structural elements in human microRNA hairpin precursors. BMC Bioinformatics. Mar. 1, 2016;17:112. doi: 10.1186/s12859-016-0960-6.

Liu et al., Targeted Degradation of the Oncogenic MicroRNA 17-92 Cluster by Structure-Targeting Ligands. J Am Chem Soc. Apr. 15, 2020;142(15):6970-6982. doi: 10.1021/jacs.9b13159. Epub Apr. 1, 2020. Author Manuscript 26 pages. Supporting information included. 78 pages total.

Ma et al., Biochemical Evaluation of a 108-Member Deglycobleomycin Library: Viability of a Selection Strategy for Identifying Bleomycin Analogues with Altered Properties. J. Am. Chem. Soc. Sep. 2007;129(41):12439-52.

Mathews et al., Incorporating chemical modification constraints into a dynamic programming algorithm for prediction of RNA secondary structure. Proc Natl Acad Sci U S A. May 11, 2004;101(19):7287-92. doi: 10.1073/pnas.0401799101. Epub May 3, 2004.

Michlewski et al., Posttranscriptional regulation of miRNAs harboring conserved terminal loops. Mol Cell. Nov. 7, 2008;32(3):383-93. doi: 10.1016/j.molcel.2008.10.013.

Milligan et al., Synthesis of small RNAs using T7 RNA polymerase. Methods Enzymol. 1989;180:51-62. doi: 10.1016/0076-6879(89)80091-6.

Mogilyansky et al., The miR-17/92 cluster: a comprehensive update on its genomics, genetics, functions and increasingly important and numerous roles in health and disease. Cell Death Differ. Dec. 2013;20(12):1603-14. doi: 10.1038/cdd.2013.125.

Mukherjee et al., PEARL-seq: A Photoaffinity Platform for the Analysis of Small Molecule-RNA Interactions. ACS Chem Biol. Sep. 18, 2020;15(9):2374-2381. doi: 10.1021/acschembio.0c00357. Epub Aug. 17, 2020.

Nakamoto et al., Diazirine-containing tag-free RNA probes for efficient RISC-loading and photoaffinity labeling of microRNA targets. Bioorg Med Chem Lett. Sep. 15, 2018;28(17):2906-2909. doi: 10.1016/j.bmcl.2018.07.020. Epub Jul. 11, 2018.

Nakamoto et al., Labeling of target mRNAs using a photo-reactive microRNA probe. Chem Commun (Camb). May 10, 2016;52(40):6720-2. doi: 10.1039/c6cc01360k.

Nguyen et al., Rationally designed small molecules that target both the DNA and RNA causing myotonic dystrophy type 1. J Am Chem Soc. Nov. 11, 2015;137(44):14180-9. doi: 10.1021/jacs.5b09266. Epub Nov. 3, 2015.

Norgren et al., On-Resin Click-Glycoconjugation of Peptoids. Synthesis. 2009;3:0488-94. Epub Jan. 9, 2009.

Osborn et al., Platinum-RNA modifications following drug treatment in S. cerevisiae identified by click chemistry and enzymatic mapping. ACS Chem Biol. Oct. 17, 2014;9(10):2404-11. doi: 10.1021/cb500395z. Epub Aug. 15, 2014.

Otsuka et al., Man-designed bleomycin with altered sequence specificity in DNA cleavage. J. Am. Chem. Soc. Jan. 1990;112(2):838-45.

Owa et al., Man-designed bleomycins: Significance of the binding sites as enzyme models and of the stereochemistry of the linker moiety. Tetrahedron. 1992;48(7):1193-208.

Parker et al., Ligand and Target Discovery by Fragment-Based Screening in Human Cells. Cell. Jan. 26, 2017;168(3):527-541.e29. doi: 10.1016/j.cell.2016.12.029. Epub Jan. 19, 2017.

Paul et al., Two-dimensional combinatorial screening and the RNA Privileged Space Predictor program efficiently identify aminoglycoside-RNA hairpin loop interactions. Nucleic Acids Res. Sep. 2009;37(17):5894-907. doi: 10.1093/nar/gkp594. Epub Sep. 2, 2009.

(56) References Cited

OTHER PUBLICATIONS

Rädle et al., Metabolic labeling of newly transcribed RNA for high resolution gene expression profiling of RNA synthesis, processing and decay in cell culture. J Vis Exp. Aug. 8, 2013;(78):50195. doi: 10.3791/50195. 11 pages.
Rupaimoole et al., MicroRNA therapeutics: towards a new era for the management of cancer and other diseases. Nat Rev Drug Discov. Mar. 2017;16(3):203-222. doi: 10.1038/nrd.2016.246. Epub Feb. 17, 2017.
Rupaimoole et al., miRNA Deregulation in Cancer Cells and the Tumor Microenvironment. Cancer Discov. Mar. 2016;6(3):235-46. doi: 10.1158/2159-8290.CD-15-0893. Epub Feb. 10, 2016. Author Manuscript, 20 pages.
Seike et al., MiR-21 is an EGFR-regulated anti-apoptotic factor in lung cancer in never-smokers. Proc Natl Acad Sci U S A. Jul. 21, 2009;106(29):12085-90. doi: 10.1073/pnas.0905234106. Epub Jul. 13, 2009.
Setny et al., Search for novel aminoglycosides by combining fragment-based virtual screening and 3D-QSAR scoring. J Chem Inf Model. Feb. 2009;49(2):390-400. doi: 10.1021/ci800361a. Author manuscript, 27 pages.
Sexton et al., Interpreting Reverse Transcriptase Termination and Mutation Events for Greater Insight into the Chemical Probing of RNA. Biochemistry. Sep. 5, 2017;56(35):4713-4721. doi: 10.1021/acs.biochem.7b00323. Epub Aug. 18, 2017. Author manuscript, 17 pages.
Shi et al., Overexpression of microRNA-96-5p inhibits autophagy and apoptosis and enhances the proliferation, migration and invasiveness of human breast cancer cells. Oncol Lett. Jun. 2017;13(6):4402-4412. doi: 10.3892/ol.2017.6025. Epub Apr. 11, 2017.
Sicard et al., Targeting miR-21 for the therapy of pancreatic cancer. Mol Ther. May 2013;21(5):986-94. doi: 10.1038/mt.2013.35. Epub Mar. 12, 2013.
Stelzer et al., Discovery of selective bioactive small molecules by targeting an RNA dynamic ensemble. Nat Chem Biol. Jun. 26, 2011;7(8):553-9. doi: 10.1038/nchembio.596. Author manuscript, 15 pages.
Stubbe et al., Mechanisms of bleomycin-induced DNA degradation. Chem. Rev. Oct. 1987;87(5):1107-36.
Suresh et al., A general fragment-based approach to identify and optimize bioactive ligands targeting RNA. Proc Natl Acad Sci U S A. Dec. 29, 2020;117(52):33197-33203. doi: 10.1073/pnas.2012217117. Epub Dec. 14, 2020.
Thakur et al., Small-molecule activators of RNase L with broad-spectrum antiviral activity. Proc Natl Acad Sci U S A. Jun. 5, 2007;104(23):9585-90. doi: 10.1073/pnas.0700590104. Epub May 29, 2007.
Thomas et al., Solid-Phase Synthesis of Bleomycin A5 and Three Monosaccharide Analogues: Exploring the Role of the Carbohydrate Moiety in RNA Cleavage. J. Am. Chem. Soc. Oct. 2002;124(44):12926-7.
Thomas et al., Targeting RNA with small molecules. Chem Rev. Apr. 2008;108(4):1171-224. doi: 10.1021/cr0681546. Epub Mar. 25, 2008.
Ule et al., CLIP identifies Nova-regulated RNA networks in the brain. Science. Nov. 14, 2003;302(5648):1212-5. doi: 10.1126/science.1090095.
Van Meter et al., A review of currently identified small molecule modulators of microRNA function. Eur J Med Chem. Feb. 15, 2020;188:112008. doi: 10.1016/j.ejmech.2019.112008. Epub Dec. 23, 2019.
Velagapudi et al., A cross-linking approach to map small molecule-RNA binding sites in cells. Bioorg Med Chem Lett. Jun. 15, 2019;29(12):1532-1536. doi: 10.1016/j.bmcl.2019.04.001. Epub Apr. 2, 2019. Author manuscript, 9 pages.
Velagapudi et al., Defining RNA-Small Molecule Affinity Landscapes Enables Design of a Small Molecule Inhibitor of an Oncogenic Noncoding RNA. ACS Cent Sci. Mar. 22, 2017;3(3):205-216. doi: 10.1021/acscentsci.7b00009. Epub Mar. 6, 2017.
Velagapudi et al., Defining the RNA Internal Loops Preferred by Benzimidazole Derivatives via 2D Combinational Screening and Computational Analysis. J Am Chem Soc. Jul. 6, 2011;133(26):10111-8. doi: 10.1021/ja200212b. Epub Jun. 9, 2011. Author manuscript, 17 pages.
Velagapudi et al., Sequence-based design of bioactive small molecules that target precursor microRNAs. Nat Chem Biol. Apr. 2014;10(4):291-7. doi: 10.1038/nchembio.1452. Epub Feb. 9, 2014. Author manuscript, 23 pages.
Velagapudi et al., Structure-activity relationships through sequencing (StARTS) defines optimal and suboptimal RNA motif targets for small molecules. Angew Chem Int Ed Engl. May 17, 2010;49(22):3816-8. doi: 10.1002/anie.200907257.
Wang et al., Mechanistic studies of a small-molecule modulator of SMN2 splicing. Proc Natl Acad Sci U S A. May 15, 2018;115(20):E4604-E4612. doi: 10.1073/pnas.1800260115. Epub Apr. 30, 2018.
Xu et al., Synthesis, biological evaluation and DNA binding properties of novel bleomycin analogues. Bioorg Med Chem Lett. Aug. 4, 2003;13(15):2595-9. doi: 10.1016/s0960-894x(03)00435-9.
Yan et al., Design, synthesis and activity of light deactivatable microRNA inhibitor. Bioorg Chem. Oct. 2018;80:492-497. doi: 10.1016/j.bioorg.2018.07.003. Epub Jul. 2, 2018. Author manuscript, 14 pages.
Yan et al., Regulating miRNA-21 Biogenesis by Bifunctional Small Molecules. J Am Chem Soc. Apr. 12, 2017;139(14):4987-4990. doi: 10.1021/jacs.7b00610. Epub Mar. 29, 2017. Author manuscript, 11 pages.
Yang et al., Design of a bioactive small molecule that targets r(AUUCU) repeats in spinocerebellar ataxia 10. Nat Commun. Jun. 1, 2016;7:11647. doi: 10.1038/ncomms11647.
Yang et al., Inhibition of Non-ATG Translational Events in Cells via Covalent Small Molecules Targeting RNA. J Am Chem Soc. Apr. 29, 2015;137(16):5336-45. doi: 10.1021/ja507448y. Epub Apr. 15, 2015. Author manuscript, 22 pages.
Yang et al., Mouse models for tumor metastasis. Methods Mol Biol. 2012;928:221-8. doi: 10.1007/978-1-62703-008-3_17. Author manuscript, 6 pages.
Zhang et al., miR-17-92 cluster and autophagy in cancer. Chinese Bulletin of Life Sciences. Nov. 2017;29(11):1149-55.
Machtel et al., Emerging applications of riboswitches—from antibacterial targets to molecular tools. J Appl Genet. Nov. 2016;57(4):531-541. doi: 10.1007/s13353-016-0341-x. Epub Mar. 28, 2016.
Manzi et al., Carbene footprinting accurately maps binding sites in protein-ligand and protein-protein interactions. Nat Commun. Nov. 16, 2016;7:13288. doi: 10.1038/ncomms13288.
Li et al., RNA as a stable polymer to build controllable and defined nanostructures for material and biomedical applications. Nano Today. Oct. 1, 2015;10(5):631-655. doi: 10.1016/j.nantod.2015.09.003. Author manuscript, 48 pages.
Smola et al., Selective 2'-hydroxyl acylation analyzed by primer extension and mutational profiling (SHAPE-MaP) for direct, versatile and accurate RNA structure analysis. Nat Protoc. Nov. 2015;10(11):1643-69. doi: 10.1038/nprot.2015.103. Epub Oct. 1, 2015. Author manuscript, 62 pages.
Yu et al., Estimating RNA structure chemical probing reactivities from reverse transcriptase stops and mutations. bioRxiv. Mar. 30, 2020. doi: https://doi.org/10.1101/292532.
U.S. Appl. No. 18/717,720, filed Jun. 7, 2024, Disney et al.
U.S. Appl. No. 17/755,105, filed Apr. 21, 2022, Disney et al.

* cited by examiner

A

1

2

3

Bleomycin A5

SEQUENCE LISTING

<160> NUMBER OF SEQ ID NOS: 35

<210> SEQ ID NO 1
<211> LENGTH: 23
<212> TYPE: DNA
<213> ORGANISM: Artificial sequence
<220> FEATURE:
<223> OTHER INFORMATION: Synthetic sequence

<400> SEQUENCE: 1
tttggcacta gcacattttt gct 23

<210> SEQ ID NO 2
<211> LENGTH: 17
<212> TYPE: DNA
<213> ORGANISM: Artificial sequence
<220> FEATURE:
<223> OTHER INFORMATION: Synthetic sequence

<400> SEQUENCE: 2
agagagcccg caccagt 17

<210> SEQ ID NO 3
<211> LENGTH: 18
<212> TYPE: DNA
<213> ORGANISM: Artificial sequence
<220> FEATURE:
<223> OTHER INFORMATION: Synthetic sequence

<400> SEQUENCE: 3
cttgaggagg agcaggct 18

<210> SEQ ID NO 4
<211> LENGTH: 23
<212> TYPE: DNA
<213> ORGANISM: Artificial sequence
<220> FEATURE:
<223> OTHER INFORMATION: Synthetic sequence

<400> SEQUENCE: 4
acacgcaaat tcgtgaagcg ttc 23

<210> SEQ ID NO 5
<211> LENGTH: 20
<212> TYPE: DNA
<213> ORGANISM: Artificial sequence
<220> FEATURE:
<223> OTHER INFORMATION: Synthetic sequence

<400> SEQUENCE: 5
gaatcgagca ccagttacgc 20

<210> SEQ ID NO 6
<211> LENGTH: 23
<212> TYPE: DNA
<213> ORGANISM: Artificial sequence
<220> FEATURE:
<223> OTHER INFORMATION: Synthetic sequence

<400> SEQUENCE: 6
taccctgtag aaccgaattt gtg 23

<210> SEQ ID NO 7
<211> LENGTH: 22
<212> TYPE: DNA
<213> ORGANISM: Artificial sequence -continued

```
<220> FEATURE:
<223> OTHER INFORMATION: Synthetic sequence

<400> SEQUENCE: 7

tagcttatca gactgatgtt ga                                              22


<210> SEQ ID NO 8
<211> LENGTH: 21
<212> TYPE: DNA
<213> ORGANISM: Artificial sequence
<220> FEATURE:
<223> OTHER INFORMATION: Synthetic sequence

<400> SEQUENCE: 8

ttcacagtgg ctaagttccg c                                               21


<210> SEQ ID NO 9
<211> LENGTH: 23
<212> TYPE: DNA
<213> ORGANISM: Artificial sequence
<220> FEATURE:
<223> OTHER INFORMATION: Synthetic sequence

<400> SEQUENCE: 9

tctttggtta tctagctgta tga                                             23


<210> SEQ ID NO 10
<211> LENGTH: 22
<212> TYPE: DNA
<213> ORGANISM: Artificial sequence
<220> FEATURE:
<223> OTHER INFORMATION: Synthetic sequence

<400> SEQUENCE: 10

tgtaacagca actccatgtg ga                                              22


<210> SEQ ID NO 11
<211> LENGTH: 22
<212> TYPE: DNA
<213> ORGANISM: Artificial sequence
<220> FEATURE:
<223> OTHER INFORMATION: Synthetic sequence

<400> SEQUENCE: 11

tagcagcaca taatggtttg tg                                              22


<210> SEQ ID NO 12
<211> LENGTH: 22
<212> TYPE: DNA
<213> ORGANISM: Artificial sequence
<220> FEATURE:
<223> OTHER INFORMATION: Synthetic sequence

<400> SEQUENCE: 12

tagcagcacg taaatattgg cg                                              22


<210> SEQ ID NO 13
<211> LENGTH: 23
<212> TYPE: DNA
<213> ORGANISM: Artificial sequence
<220> FEATURE:
<223> OTHER INFORMATION: Synthetic sequence

<400> SEQUENCE: 13

tctacagtgc acgtgtctcc agt                                             23
```

-continued

<210> SEQ ID NO 14
<211> LENGTH: 24
<212> TYPE: DNA
<213> ORGANISM: Artificial sequence
<220> FEATURE:
<223> OTHER INFORMATION: Synthetic sequence

<400> SEQUENCE: 14
tttggcaatg gtagaactca cact 24

<210> SEQ ID NO 15
<211> LENGTH: 22
<212> TYPE: DNA
<213> ORGANISM: Artificial sequence
<220> FEATURE:
<223> OTHER INFORMATION: Synthetic sequence

<400> SEQUENCE: 15
taggtagttt catgttgttg gg 22

<210> SEQ ID NO 16
<211> LENGTH: 21
<212> TYPE: DNA
<213> ORGANISM: Artificial sequence
<220> FEATURE:
<223> OTHER INFORMATION: Synthetic sequence

<400> SEQUENCE: 16
tcacagtgaa ccggtctctt t 21

<210> SEQ ID NO 17
<211> LENGTH: 23
<212> TYPE: DNA
<213> ORGANISM: Artificial sequence
<220> FEATURE:
<223> OTHER INFORMATION: Synthetic sequence

<400> SEQUENCE: 17
tgtagtgttt cctactttat gga 23

<210> SEQ ID NO 18
<211> LENGTH: 21
<212> TYPE: DNA
<213> ORGANISM: Artificial sequence
<220> FEATURE:
<223> OTHER INFORMATION: Synthetic sequence

<400> SEQUENCE: 18
tgtcagtttg tcaaataccc c 21

<210> SEQ ID NO 19
<211> LENGTH: 21
<212> TYPE: DNA
<213> ORGANISM: Artificial sequence
<220> FEATURE:
<223> OTHER INFORMATION: Synthetic sequence

<400> SEQUENCE: 19
tacagtactg tgataactga a 21

<210> SEQ ID NO 20
<211> LENGTH: 22
<212> TYPE: DNA
<213> ORGANISM: Artificial sequence
<220> FEATURE:
<223> OTHER INFORMATION: Synthetic sequence

<400> SEQUENCE: 20
taacagtcta cagccatggt cg 22

<210> SEQ ID NO 21
<211> LENGTH: 21
<212> TYPE: DNA
<213> ORGANISM: Artificial sequence
<220> FEATURE:
<223> OTHER INFORMATION: Synthetic sequence

<400> SEQUENCE: 21
taacagtctc cagtcacggc c 21

<210> SEQ ID NO 22
<211> LENGTH: 23
<212> TYPE: DNA
<213> ORGANISM: Artificial sequence
<220> FEATURE:
<223> OTHER INFORMATION: Synthetic sequence

<400> SEQUENCE: 22
tatggctttt tattcctatg tga 23

<210> SEQ ID NO 23
<211> LENGTH: 22
<212> TYPE: DNA
<213> ORGANISM: Artificial sequence
<220> FEATURE:
<223> OTHER INFORMATION: Synthetic sequence

<400> SEQUENCE: 23
cttggcacct agcaagcact ca 22

<210> SEQ ID NO 24
<211> LENGTH: 81
<212> TYPE: DNA
<213> ORGANISM: Artificial sequence
<220> FEATURE:
<223> OTHER INFORMATION: Synthetic sequence

<400> SEQUENCE: 24
gggtggccga ttttggcact agcacatttt tgcttgtgtc tctccgctct gagcaatcat 60
gtgcagtgcc aatatgggaa a 81

<210> SEQ ID NO 25
<211> LENGTH: 44
<212> TYPE: DNA
<213> ORGANISM: Artificial sequence
<220> FEATURE:
<223> OTHER INFORMATION: Synthetic sequence

<400> SEQUENCE: 25
ggccggatcc taatacgact cactataggg tggccgattt tggc 44

<210> SEQ ID NO 26
<211> LENGTH: 15
<212> TYPE: DNA
<213> ORGANISM: Artificial sequence
<220> FEATURE:
<223> OTHER INFORMATION: Synthetic sequence

<400> SEQUENCE: 26
tttcccatat tggca 15

-continued

<210> SEQ ID NO 27
<211> LENGTH: 38
<212> TYPE: DNA
<213> ORGANISM: Artificial sequence
<220> FEATURE:
<223> OTHER INFORMATION: Synthetic sequence

<400> SEQUENCE: 27
cagacgtgtg ctcttccgat ctcgcagctg cgggtcct 38

<210> SEQ ID NO 28
<211> LENGTH: 22
<212> TYPE: DNA
<213> ORGANISM: Artificial sequence
<220> FEATURE:
<223> OTHER INFORMATION: Synthetic sequence

<400> SEQUENCE: 28
agatcggaag agcgtcgtgt ag 22

<210> SEQ ID NO 29
<211> LENGTH: 21
<212> TYPE: DNA
<213> ORGANISM: Artificial sequence
<220> FEATURE:
<223> OTHER INFORMATION: Synthetic sequence

<400> SEQUENCE: 29
cagacgtgtg ctcttccgat c 21

<210> SEQ ID NO 30
<211> LENGTH: 22
<212> TYPE: DNA
<213> ORGANISM: Artificial sequence
<220> FEATURE:
<223> OTHER INFORMATION: Synthetic sequence

<400> SEQUENCE: 30
ctacacgacg ctcttccgat ct 22

<210> SEQ ID NO 31
<211> LENGTH: 77
<212> TYPE: RNA
<213> ORGANISM: Artificial Sequence
<220> FEATURE:
<223> OTHER INFORMATION: A synthetic oligonucleotide sequence

<400> SEQUENCE: 31
uggccgauuu ggcacuagca cauuuuugcu ugugucucuc cgcucugagc aaucaugugc 60
agugccaaua ugggaaa 77

<210> SEQ ID NO 32
<211> LENGTH: 65
<212> TYPE: RNA
<213> ORGANISM: Artificial Sequence
<220> FEATURE:
<223> OTHER INFORMATION: A synthetic oligonucleotide sequence

<400> SEQUENCE: 32
uuuggcacua gcacauuuuu gcuugugucu cuccgcucug agcaaucaug ugcagugcca 60
auaug 65

<210> SEQ ID NO 33
<211> LENGTH: 21

-continued

```
<212> TYPE: RNA
<213> ORGANISM: Artificial Sequence
<220> FEATURE:
<223> OTHER INFORMATION: A synthetic oligonucleotide sequence

<400> SEQUENCE: 33

uuugcacuag cacauuuuug c                                              21


<210> SEQ ID NO 34
<211> LENGTH: 10
<212> TYPE: RNA
<213> ORGANISM: Artificial Sequence
<220> FEATURE:
<223> OTHER INFORMATION: A synthetic oligonucleotide sequence

<400> SEQUENCE: 34

aaaaaaaaaa                                                           10


<210> SEQ ID NO 35
<211> LENGTH: 86
<212> TYPE: DNA
<213> ORGANISM: Artificial Sequence
<220> FEATURE:
<223> OTHER INFORMATION: A synthetic oligonucleotide sequence

<400> SEQUENCE: 35

ggtcctgctt ttcccatatt ggcactgcac atgattgctc agagcggaga gacacaagca     60

aaaatgtgct agtgagatcg gaagag                                         86
```

TARGET VALIDATION AND PROFILING OF THE RNA TARGETS OF SMALL MOLECULES

PRIORITY CLAIM TO RELATED APPLICATIONS

This application is a U.S. national stage filing under 35 U.S.C. § 371 from International Application No. PCT/US2019/053179, filed on 26 Sep. 2019, and published as WO2020/076511 on 16 Apr. 2020, which claims the benefit under 35 U.S.C. 119 (e) to U.S. Provisional Application No. 62/743,996, filed on 10 Oct. 2018, the benefit of priority of each of which is claimed herein, and which applications and publication are hereby incorporated herein by reference in their entirety.

STATEMENT OF GOVERNMENT SUPPORT

This invention was made with government support under grant number GM097455 awarded by the National Institutes of Health. The government has certain rights in the invention.

BACKGROUND

ENCODE showed that over 70% of our genome is transcribed into RNA[1]. These RNAs have diverse functions, particularly those that are non-coding[1]. Small molecule targeting of RNA, however, has been challenging, except for RNAs that fold into highly three-dimensional (protein-like) structures such as ribosomes and riboswitches[2-4]. More recently, it has been shown that pre-mRNAs in complexes can be targeted and stabilized with small molecules[5-6]. Most RNAs, however, do not have highly complex long-range folds but do have extensive two-dimensional (secondary) structure that that could be targeted with small molecules[7-8]. Indeed, small molecules have been discovered that bind microRNAs (miRNAs) and inhibit their biogenesis[9-11].

SUMMARY

The invention is directed, in various embodiments, to a method of mapping an RNA binding site of an RNA-binding small molecule, the binding site being disposed within an RNA sequence library, comprising contacting the RNA of the sequence library and an effective amount of a compound comprising a conjugate of an RNA-cleaving moiety and an RNA-binding small molecule to cleave the RNA of the sequence library comprising the binding site to provide a cleaved RNA fragment;

then, amplifying and sequencing the cleaved RNA fragment, thereby identifying the site of binding within the RNA sequence library of the small RNA-binding molecule associated with the site of cleavage;

to identify the sequence of the RNA binding site of the small RNA-binding molecule.

In various cases, the methods disclosed herein comprise contacting a library of RNA sequences and an effective amount of a compound comprising a conjugate of an RNA-cleaving moiety and an RNA-binding small molecule to cleave the RNA of the library at a binding site of the compound to the RNA to provide a cleaved RNA fragment; and amplifying and sequencing the cleaved RNA fragment, thereby identifying the site of binding of the small RNA-binding molecule to the RNA of the library which is associated with the site of cleavage.

For example, the RNA-binding small molecule can comprise an N-methyl-piperazinyl-bis-benzimidazole group. For example, the conjugate of the RNA-binding molecule can comprise bleomycin, for instance bleomycin A5, as the RNA-cleaving moiety. In some embodiments, the RNA-binding molecule can be Targaprimir-96.

In various embodiments, a method of the invention comprises precisely targeting cellular destruction of an oncogenic non-coding RNA precursor, comprising contacting a cell expressing the non-coding RNA precursor and an effective amount of the compound. For instance, the oncogenic non-coding RNA precursor can comprise oncogenic primary microRNA-96 (pri-miR-96). More specifically, the compound can be a covalent conjugate of Targaprimir-96 and bleomycin A5.

In various embodiments, a methods comprise enhancing expression of FOXO1 protein in breast cancer cells, comprising contacting the cells with an effective amount of the conjugate. For example, the contacting can be via administration to a human patient. More specifically, the conjugate can be a covalent conjugate of Targaprimir-96 and bleomycin A5.

In various embodiments, a method of the invention can comprise triggering apoptosis in triple negative breast cancer cells, comprising contacting the cells with an effective amount of the conjugate. The breast cancer cells can be present in a human patient. The conjugate can be a covalent conjugate of Targaprimir-96 and bleomycin A5.

In various embodiments, methods comprise treating triple negative breast cancer, comprising administering to a patient afflicted therewith an effective dose of the compound. For example, the breast cancer can comprise expression of oncogenic primary microRNA-96 (pri-miR-96). The compound can be a covalent conjugate of Targaprimir-96 and bleomycin A5.

In various embodiments, the RNA sequence library can comprise a transcriptome. For example, the transcriptome can be viral, or can be mammalian, or can be bacterial. The RNA sequence library can comprise one or more of synthetic, semi-synthetic, or natural RNA. The RNA sequence library can comprise the genome of an RNA virus.

In various embodiments, a method of the invention can be carried out in vitro, or can be carried out in living cells, e.g., in virally- or bacterially-infected cells.

In various embodiments of a method of the invention, a set of RNA sequences and a set of compounds comprising candidate RNA-binding small molecules can be assayed in a 2-dimensional parallel array.

The invention further provides a compound comprising a conjugate of an RNA-cleaving moiety and an RNA-binding small molecule. The RNA-cleaving moiety can comprise bleomycin. The RNA-binding small molecule can comprise N-methyl-piperazinyl-bis-benzimidazole group, e.g., Targaprimir-96.

DETAILED DESCRIPTION

To provide rational approaches to target RNA with small molecules, we developed a sequence-based approach dubbed Inforna[12]. In particular, Informa enabled the design of a small molecule (Targaprimir-96, 1, FIG. 1A) that selectively targets the Drosha endonuclease-processing site of oncogenic primary microRNA-96 (pri-miR-96)[13]. MiRNAs are non-coding RNAs that play pervasive roles in biology, and their aberrant expression or mutation can be causative of disease. They are initially produced as precursors (pri-miRNA) that are processed by the nuclease Drosha followed by translocation to the cytoplasm as precursor microRNAs (pre-miRNAs). Pre-miRNAs are cleaved by the cytoplasmic nuclease Dicer to produce mature miRNAs that bind to the 3' untranslated regions (UTRs) of mRNAs and repress translation. Application of 1 to triple negative breast cancer (TNBC) cells inhibited the production of mature miR-96, de-repressed pro-apoptotic transcription factor Forkhead box protein O1 (FOXO1) that the miRNA repressed, and triggered apoptosis (FIG. 1B)[13].

Figure 1:
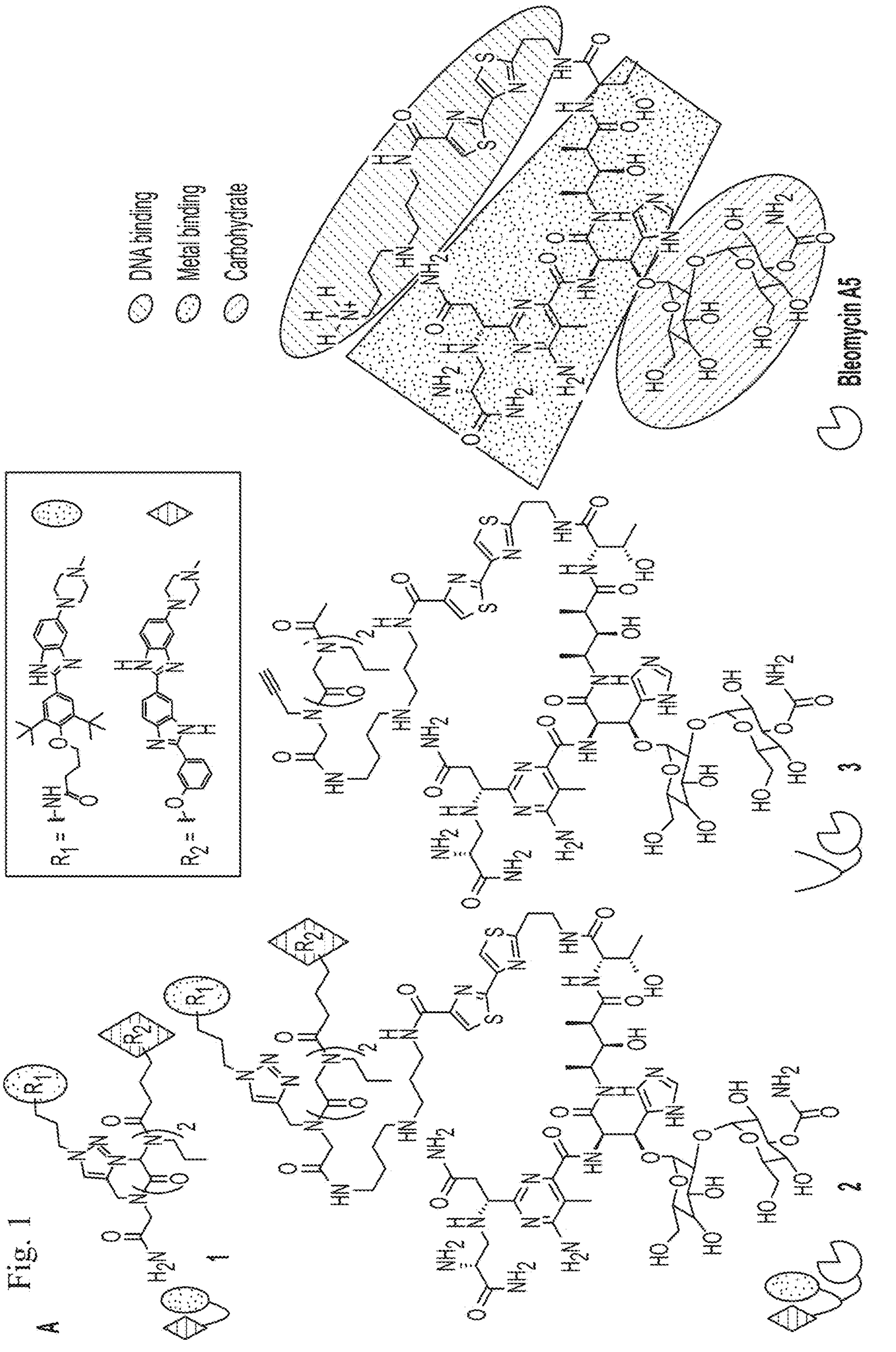
FIG. 1. Pri-miR-96 is oncogenic and suppresses apoptosis in cancer cells via repression of the pro-apoptotic transcription factor Forkhead box protein O1 (FOXO1). (A) structures of the compounds used in these studies. Compound 1 was designed via Inforna and selectively targets pri-miR-96. Compound 2 is a version of 1 conjugated to bleomycin A5 while compound 3 is a version of 2 that lacks RNA-binding modules. (B) secondary structure of pri-miR-96 and the miR-96-FOXO1 pathway. Compound binding sites are indicated in the secondary structure, and mature miR-96 is indicated in red lettering. The red "X" indicates inhibition of Drosha processing by a small molecule; likewise the red arrow indicates that inhibition of pri-miR-96 processing inhibits repression of FOXO1 and hence breast cancer. Compound 1 inhibited the production of mature miR-96, de-repressed a downstream target, pro-apoptotic transcription factor FOXO1, and triggered apoptosis. (SEQ ID NOs: 31-34)
Figure 1:
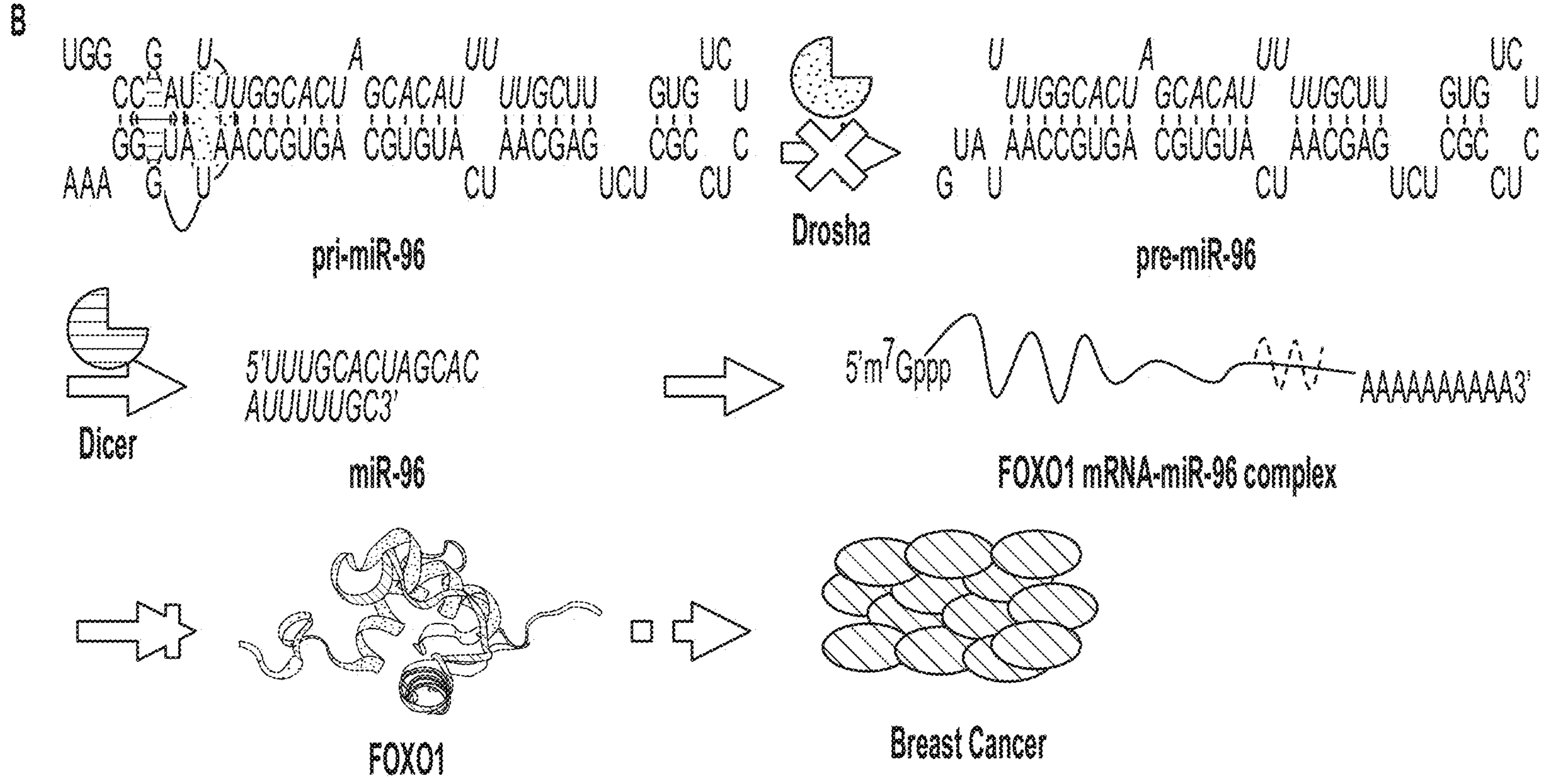

To expand the functional repertoire of small molecules that target RNA from simple binding to selective cleavage, bleomycin A5 was conjugated to 1, affording 2 (FIG. 1). Bleomycin, a natural product used for treatment of cancer, cleaves DNA[14, 15] but also cleaves RNA, as pioneered by the Hecht group[16, 17]. Bleomycin contains four domains: (i) a metal ion-binding domain that activates $O_2$ and leads to nucleic acid cleavage[18-21]; (ii) a DNA-binding domain, which affects cleavage efficiency[22]; (iii) a linker region between the metal ion-binding and DNA-binding domains, which also affects cleavage efficiency[23-27]; and (iv) a carbohydrate domain which facilitates cellular uptake[20]. We chose bleomycin A5 as the cationic dimethyl sulfonium in the C-terminal DNA-binding domain has been replaced with a butyl-1,4-diamine side chain. This modification serves two purposes: (i) facile conjugation of the terminal primary amine to RNA-binding modules containing carboxylates. Notably, acylation of the butyl-1,4-diamine side chain (cationic) with a small molecule affords an uncharged linkage; and (ii) reduction of DNA binding affinity[28-30] as the cationic side chain, known to drive binding to DNA, has been acylated and is no longer charged. In addition, it has been shown that increasing the size and hydrophobicity of bleomycin A5's butyl-1,4-diamine side chain further decreases DNA binding affinity and the extent of cleavage[28-30]. Conjugation of an RNA-binding module is therefore likely to alter bleomycin A5's binding and cleavage preferences toward RNA, as we have observed in the selective cleavage of expanded r(CUG) repeats[31].

The secondary structure of oncogenic pri-miR-96[32] was analyzed to determine if it might be a suitable target for bleomycin-mediated cleavage (FIG. 1B). Previously, it has been shown that bleomycin can cleave AU pairs in RNA[33], and indeed AU pairs are present adjacent to pri-miR-96's Drosha site. Thus, conjugation of bleomycin to compound 1 could provide a selective cleaving small molecule, provided that the bleomycin is positioned towards these AU pairs. As previous studies have shown that the 3,5-di-tert-butylbenzyl benzimidazole module in 1 binds the 1×1 UU internal loop in the Drosha site (teal oval; FIG. 1)[12], conjugation of bleomycin A5 to 1 (2; FIG. 1A) places the cleaving module near the neighboring AU pairs. Control compound 3 (FIG. 1A), which lacks the RNA-binding modules, was also synthesized.

Figure 2:
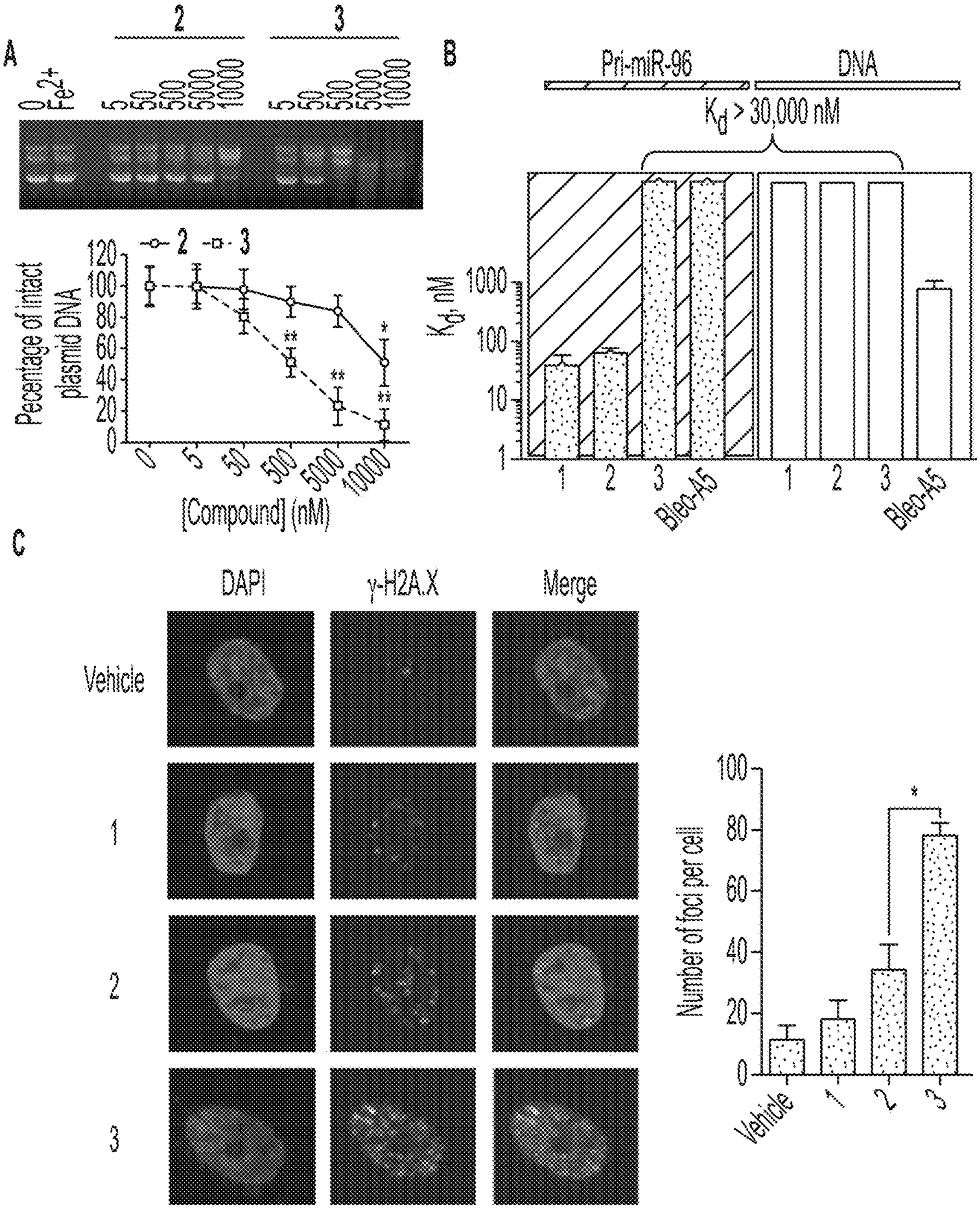
FIG. 2. DNA cleavage by 2 and 3 in vitro and in cells. (A) studying the DNA cleaving activity of 2 and 3 in vitro. Appending RNA-binding modules onto the bleomycin core (affording 2) decreased the amount of DNA cleavage as compared to 3, which lacks RNA-binding modules. (B) Visualization and quantification of DNA damage in MDA-MB-231 cells treated with 500 nM 1, 2 or 3 for 12 h. (C) 3 caused ~2.3-fold more DNA damage than 2 (500 nM of 2 or 3) as calculated by comparing the average foci number per cell for each compound. Data are expressed as mean±s.e.m. (n≥3). *$p<0.05$, as determined by a two-tailed Student t test by comparison to untreated DNA (A) or cells (B).

The sites of cleavage by 2 and 3 were studied in vitro by using primer extension with a radioactively labeled primer after reaction. In the presence of 2 and $Fe^{2+}$, a site of selective cleavage was observed adjacent to the Drosha site, as predicted; that is, cleavage at this site was not observed when pri-miR-96 was treated with $Fe^{2+}$ alone or 3 and $Fe^{2+}$. To further assess the ability of 2 and 3 to cleave nucleic acids, they were tested for cleaving DNA. As shown in FIG. 2A, 2 cleaved DNA with 5-fold lower efficiency than 3 at concentrations≥500 nM, as calculated by comparing the percentage of DNA plasmid cleaved by both compounds ($p<0.05$). That is, conjugation of bleomycin to an RNA binder significantly reduced its ability to cleave DNA in vitro, as expected based on previous reports[30]. To confirm our in vitro cleavage results, we measured the affinities of 1, 2, 3 and bleomycin A5 for pri-miR-96 and DNA by microscale thermophoresis (MST)[34, 35] (FIG. 2B). In agreement with in vitro cleavage studies, 1 and 2 bound avidly to pri-miR-96 with $K_d$s of 39±18 nM and 64±11 nM, respectively, while saturable binding to 3 and bleomycin A5 was not observed ($K_d$>30 μM). In contrast, no saturable binding of 1, 2, or 3 to DNA was observed ($K_d$>30 μM); however, bleomycin A5 bound DNA with a $K_d$ of ~1 μM. Collectively, these results indicate that modification of bleomycin A5's side chain, whether by an RNA-binding module or a peptoid linker, greatly reduced its affinity for DNA as expected[30] and that 2 selectively bound pri-miR-96 in the low nM concentration range.

This phenomenon was also observed in cells, as studied by assessing DNA damage using an antibody for gamma H2A histone family, member X (γ-H2A.X)[36], a marker for DNA double stranded breaks visualized as nuclear foci. In agreement with in vitro DNA cleavage (FIG. 2A), 3 caused ~2.3-fold more DNA damage than 2 (500 nM of 2 or 3; FIG. 2C), as calculated by comparing the average foci number per cell for each compound. Collectively, these data show that pri-miR-96 can be cleaved to a greater extent by 2 than DNA is cleaved within a concentration window; that is, the targets that are cleaved by bleomycin can be attenuated by addition of an RNA-binding module at mid-nanomolar concentrations both in vitro and in cells, vide infra.

Figure 3:
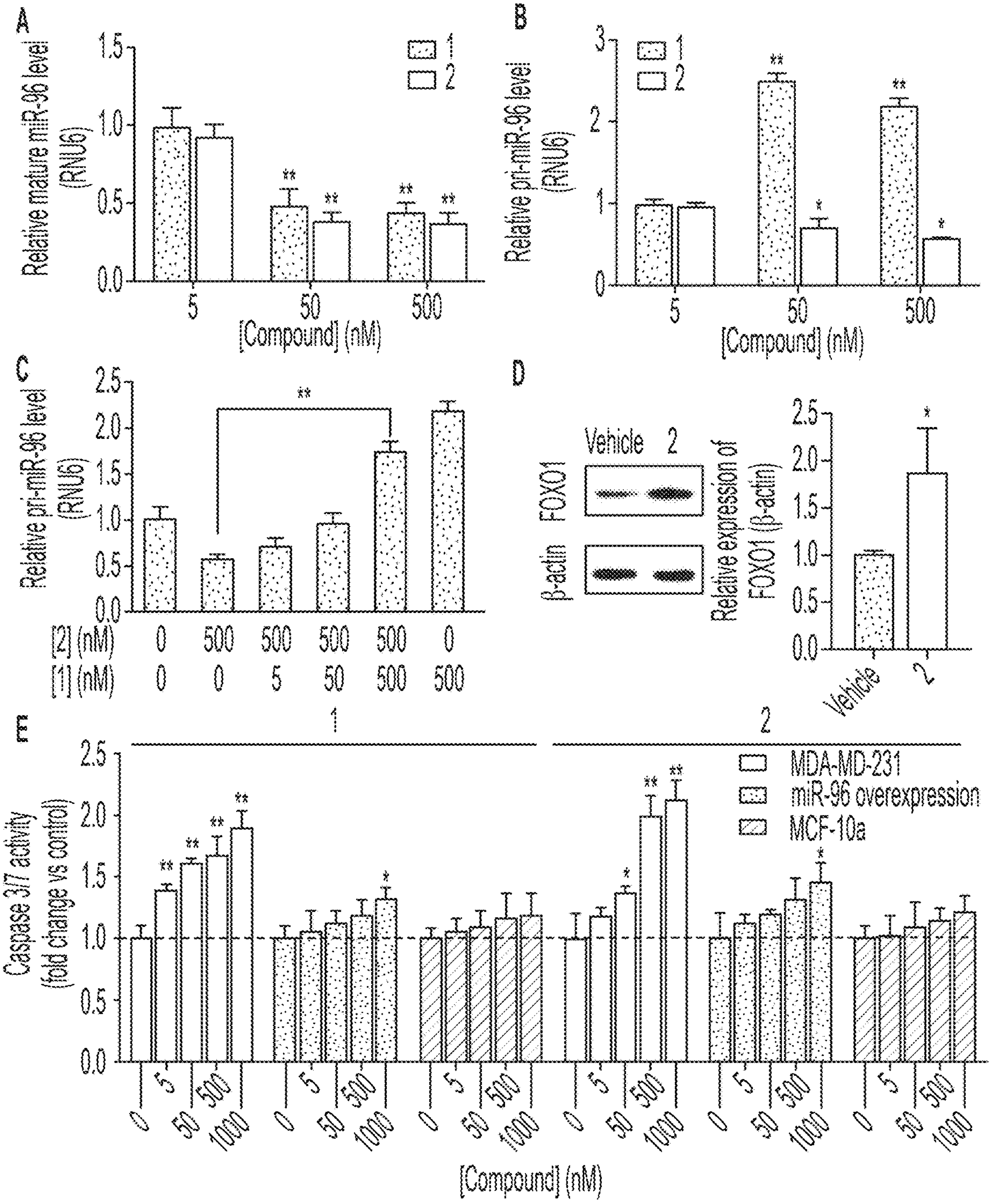
FIG. 3. Studying the effect of 1 and 2 on mature miR-96 and pri-miR-96 levels and on miRNA-mediated biology. (A) the effect of 1 and 2 on mature miR-96 levels in MDA-MB-231 TNBC cells. (B) the effect of 1 and 2 on pri-miR-96 levels in MDA-MB-231 cells. As expected based on their modes of action, 1 (simple binding) increased pri-miR-96 levels, while 2 (cleavage) reduced them. (C) co-addition of increasing concentrations of 1 (5 to 500 nM) and a constant concentration of 2 (500 nM) to MDA-MB-231 cells increased levels of pri-miR-96, diminishing the cleaving capacity of 2 as expected. (D) effect of 2 on expression of FOXO1 protein, a direct target of miR-96, as determined by Western blot. (E) effect of 2 on apoptosis in MDA-MB-231 cells (red), MDA-MB-231 cells that overexpress pri-miR-96 via a plasmid (green), and in MCF-10a healthy breast cells (blue), as determined by Caspase assays. Data are expressed as mean±s.e.m. (n≥3). *$p<0.05$, **$p<0.01$, as measured by a two-tailed Student t test by comparison to untreated cells.

Next, the effect of 2 on pri-miR-96 and mature miR-96 levels in MDA-MB-231 TNBC cells was measured via RT-qPCR. To study the cleaving effects of 2, the compound was first complexed with $Fe^{2+}$ (1 equivalent), diluted into growth medium, and then added to cells. While both compounds reduced mature miR-96 levels (FIG. 3A), 1 increased level of pri-miR-96 while 2 decreased them (FIG. 3B), as expected based on their designed mode of action, simple binding and cleavage, respectively. When 2 is prepared in the absence of $Fe^{2+}$, no statistically significant effect was observed on pri-miR-96 levels; mature miR-96 levels were reduced upon treatment with 500 nM compound as expected based on 2's binding properties ($p<0.05$). These data suggest that the cleavage of pri-miR-96 contributes to the downregulation of mature miR-96. Control compound 3 had no effect on mature or pri-miR-96 levels. To further confirm 2's mode of action, a competition cleavage experiment was completed in which increasing concentrations of 1 and a constant concentration of 2 were delivered to MDA-MB-231 cells. Both compounds show similar levels of cell permeability at 500 nM as determined by flow cytometry. Results show that the cleavage caused by 2 is effectively competed off when 1 was added (FIG. 3C). Each of these results supports the hypothesis that 2 is targeting pri-miR-96 for destruction.

In cancer cells, miR-96 suppresses apoptosis by silencing the production of pro-apoptotic transcription factor FOXO1[32]. Thus, inhibition of miR-96 by 2 should increase the amount of FOXO1 and trigger apoptosis. Indeed, the amount of FOXO1 protein in MDA-MB-231 cells was increased by ~1.8-fold when treated with 500 nM of 2 (FIG. 3D). The effect of 2 on phenotype (suppression of apoptosis)[12, 13, 32] was then assessed by using both Annexin/PI staining and Caspase assays. Importantly, 2 induced apoptosis in MDA-MB-231 cells (FIG. 3E (red)) and had no effect on MCF-10a healthy breast epithelial cells in which pri-miR-96 is not expressed in measurable amounts (FIG. 3E, blue). Further, the apoptotic effect of 2 was reduced in cells in which pri-miR-96 was overexpressed from a plasmid (FIG. 3E, green). We also measured the effect of 2 on other miRNAs, including miR-10b, which was previously shown to be a target of bleomycin A5[33], oncogenic miR-21[37], and all other miRNAs predicted to target the FOXO1 3' untranslated region (UTR) by TargetScan[38]. None of these targets was affected.

Figure 4:
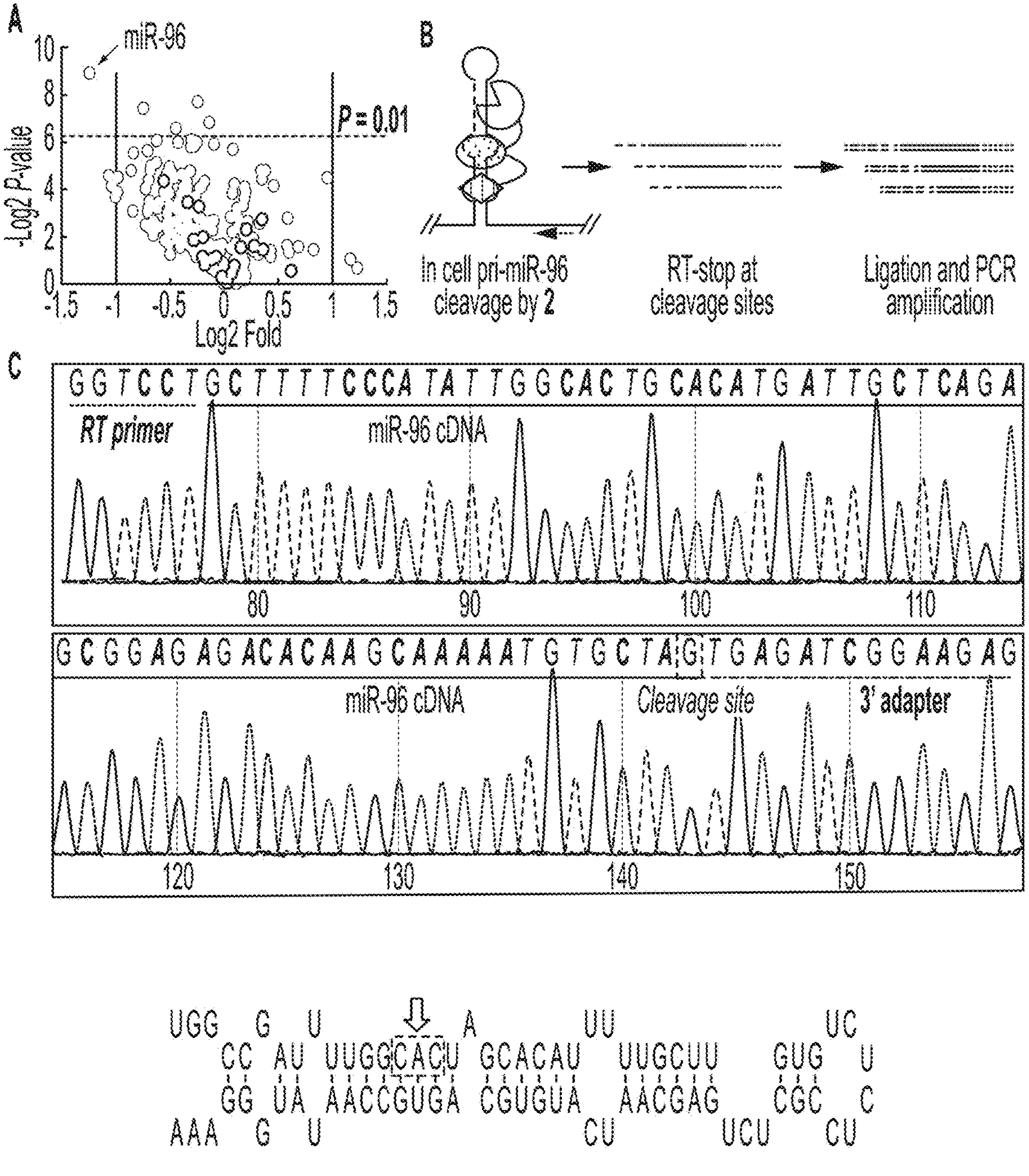
FIG. 4. An unbiased miRNA-profiling approach shows that 2 most significantly affects mature miR-96 levels in MDA-MB-231 cells and amplification of cleavage products identifies the small molecule binding site within pri-miR-96. (A) Volcano plot for profiling the effect of 2 on all expressed miRNAs in MDA-MB-231 cells; miR-96 is the most affected. (B) a scheme of the amplification approach to identify small molecule binding sites via cleavage. (C) Top, representative Sanger sequencing results from cDNA of the cleaved RNA. The cleavage site is indicated with a red box. Bottom, analysis of several clones reveals three cleavage sites (indicated with a box and arrow in the pri-miR-96 secondary structure); 40% of reads stop at the first C (5'); ~30% of reads stop at the A; and ~30% of reads stop the second C (3'). Data are expressed as mean±s.e.m. (n≥3). (SEQ ID NOs: 31 and 35)

One of the beauties of antisense is that the oligonucleotide's on- and off-targets can be inferred by depletion of an RNA's levels. To determine whether 2 can be used in target profiling studies akin to antisense, an unbiased profiling experiment (RiboSNAP; small molecule nucleic acid profiling by cleavage applied to RNA) on the 349 miRNAs expressed in MDA-MB-231 cells was completed. The data from these studies are presented as a volcano plot, a logarithmic plot of fold change vs. statistical significance (FIG. 4A). Importantly, these studies show: (i) miR-96 levels were affected to the greatest extent and were the most statistically significant, illustrating 2's remarkable selectivity. This result is of great interest considering that 2's mode of action is RNA cleavage. Evidently, conjugation of bleomycin A5 to 1 does not alter 1's selectivity[13]; (ii) small molecule-bleomycin conjugates can be used in cellular target profiling studies; and (iii) the RNA targets cleaved in cells by bleomycin can be precisely programmed by conjugation to a selective RNA small molecule binder. One challenge in developing chemical probes targeting RNA has been the perception that compounds cannot be selective, and these studies suggest that small molecules, even those that cleave, can be selective for an RNA target.

The most common method to identify small molecule binding sites within an RNA is to monitor sites of protection from nuclease cleavage or reaction with chemical modification reagents. Indeed, this approach identified sites in the ribosome that bound antibiotics[39, 40], However, some binding sites can be silent due to lack of reactivity with a chemical modifier and can require long residence times of the small molecule to prevent reactivity (irreversible). Thus, careful tuning of the experimental conditions is often necessary. Although laborious, these types of experiments are invaluable to validate or identify the target(s) of small molecules, which is essential to establish a compound's mode of action.

We posited that analyzing the cleavage footprints of 2 from RNA harvested from treated cells could identify the precise binding site, an approach we named Ribo-SNAP-Map. If cleavage sites could be amplified, both the small molecule's RNA target (Ribo-SNAP) and the binding site within the RNA (Ribo-SNAP-Map) could be identified quickly after compound treatment.

To implement Ribo-SNAP-Map, we developed a procedure to enrich the partial cleavage products of pri-miR-96 (FIG. 4B) using a gene specific forward primer and a universal reverse primer in an RT-qPCR experiment[41]. Gel analysis showed a new band at ca. 130 base pairs only when cells were exposed to 2, not to 1 or 3. Sequencing analysis confirmed that the cleavage sites were proximal to the predicted and in vitro mapped binding sites for 2 (FIG. 4C). Molecular modeling of 2 binding with pri-miR-96 also showed that 2 positions the cleaving moiety towards the AU sequence that is cleaved rather than other regions in the RNA that are distant from the ligand's binding site. Thus, Ribo-SNAP-Map can indeed be used to map binding sites in cells. Notably, AU pairs proximal to a small molecule's binding site is not requisite for selective cleavage of bleomycin A5 conjugates, as observed for r(CUG) repeats[31].

Previous studies have provided small molecules that cleave RNA by using light[42], are nuclease mimics[43], or recruit endogenous nucleases to an RNA target. In the first approach, applicability can be limited because of the necessity of light to penetrate cells and tissue. Compounds that act as nuclease mimics interact with an expanded repeating RNA and have a mixed mode of inhibition (transcriptional inhibition, inhibition of protein binding, and cleavage)[43]. Notably, expanded repeating RNAs are atypical targets; due to its repeating nature and hence multiple small molecule binding sites, inefficient cleavage could afford a significant biological effect. More recently, we developed an approach named Ribonuclease targeting chimeras (RIBOTACs) to recruit endogenous RNase L to cleave a desired RNA target[44]. However, cleavage patterns on the RNA target using these methods can be complex and may not be proximal to the binding site. In contrast, cleavage with 2 is proximal and not complex, allowing straightforward identification of RNA sequences nearby ligand binding sites.

Herein, we showed that small molecules can be engendered with antisense-like properties in cells using chimeric compounds comprised of a selective RNA-binding small molecule and bleomycinA5 as a cleaving moiety. Indeed, these studies and others suggest that: (i) the targets cleaved by bleomycin can be tuned by conjugation to an RNA-binding small molecule; (ii) these capacities are likely programmable; and (iii) the ability to cleave RNAs with small molecules could expand the target scope of ligands that modulate the biology of RNA, akin to the revolution that PROTACs[45] initiated in the protein targeting field. Most RNAs' biology may not be affected by simple binding and engendering a small molecule with the ability to cleave will likely expand the number of RNAs that can be targeted with organic compounds.

DOCUMENTS CITED 1. (2012) An integrated encyclopedia of DNA elements in the human genome. *Nature* 489, 57-74.
2. Tenson, T., and Mankin, A. (2006) Antibiotics and the ribosome. *Mol. Microbiol.* 59, 1664-1677.
3. Howe, J. A., Wang, H., Fischmann, T. O., Balibar, C. J., Xiao, L., Galgoci, A. M., Malinverni, J. C., Mayhood, T., Villafania, A., Nahvi, A., Murgolo, N., Barbieri, C. M., Mann, P. A., Carr, D., Xia, E., Zuck, P., Riley, D., Painter, R. E., Walker, S. S., Sherborne, B., de Jesus, R., Pan, W., Plotkin, M. A., Wu, J., Rindgen, D., Cummings, J., Garlisi, C. G., Zhang, R., Sheth, P. R., Gill, C. J., Tang, H., and Roemer, T. (2015) Selective small-molecule inhibition of an RNA structural element. *Nature* 526, 672-677.
4. Ratmeyer, L. S., Vinayak, R., Zon, G., and Wilson, W. D. (1992) An ethidium analogue that binds with high specificity to a base-bulged duplex from the TAR RNA region of the HIV-I genome. *J. Med. Chem.* 35, 966-968.
5. Naryshkin, N. A., Weetall, M., Dakka, A., Narasimhan, J., Zhao, X., Feng, Z., Ling, K. K., Karp, G. M., Qi, H., Woll, M. G., Chen, G., Zhang, N., Gabbeta, V., Vazirani, P., Bhattacharyya, A., Furia, B., Risher, N., Sheedy, J., Kong, R., Ma, J., Turpoff, A., Lee, C. S., Zhang, X., Moon, Y. C., Trifillis, P., Welch, E. M., Colacino, J. M., Babiak, J., Almstead, N. G., Peltz, S. W., Eng, L. A., Chen, K. S., Mull, J. L., Lynes, M. S., Rubin, L. L., Fontoura, P., Santarelli, L., Haehnke, D., McCarthy, K. D., Schmucki, R., Ebeling, M., Sivaramakrishnan, M., Ko, C. P., Paushkin, S. V., Ratni, H., Gerlach, I., Ghosh, A., and Metzger, F. (2014) Motor neuron disease. SMN2 splicing modifiers improve motor function and longevity in mice with spinal muscular atrophy. *Science* 345, 688-693.
6. Palacino, J., Swalley, S. E., Song, C., Cheung, A. K., Shu, L., Zhang, X., Van Hoosear, M., Shin, Y., Chin, D. N., Keller, C. G., Beibel, M., Renaud, N. A., Smith, T. M., Salcius, M., Shi, X., Hild, M., Servais, R., Jain, M., Deng, L., Bullock, C., McLellan, M., Schuierer, S., Murphy, L., Blommers, M. J., Blaustein, C., Berenshteyn, F., Lacoste, A., Thomas, J. R., Roma, G., Michaud, G. A., Tseng, B. S., Porter, J. A., Myer, V. E., Tallarico, J. A., Hamann, L. G., Curtis, D., Fishman, M. C., Dietrich, W. F., Dales, N. A., and Sivasankaran, R. (2015) SMN2 splice modulators enhance U1-pre-mRNA association and rescue SMA mice. *Nat. Chem. Biol.* 11, 511-517.
7. Lu, Z., and Chang, H. Y. (2016) Decoding the RNA structurome. *Curr. Opin. Struct. Biol.* 36, 142-148.
8. Bevilacqua, P. C., Ritchey, L. E., Su, Z., and Assmann, S. M. (2016) Genome-wide analysis of RNA secondary structure. *Ann. Rev. Genet.* 50, 235-266.
9. Im, K., Song, J., Han, Y. T., Lee, S., Kang, S., Hwang, K. W., Min, H., and Min, K. H. (2017) Identification of aminosulfonylarylisoxazole as microRNA-31 regulators. *PLoS One* 12, e0182331.
10. Yan, H., Bhattarai, U., Song, Y., and Liang, F. S. (2018) Design, synthesis and activity of light deactivatable microRNA inhibitor. *Bioorg. Chem.* 80, 492-497.
11. Yan, H., Bhattarai, U., Guo, Z. F., and Liang, F. S. (2017) Regulating miRNA-21 biogenesis by bifunctional small molecules. *J. Am. Chem. Soc.* 139, 4987-4990.
12. Velagapudi, S. P., Gallo, S. M., and Disney, M. D. (2014) Sequence-based design of bioactive small molecules that target precursor microRNAs. *Nat. Chem. Biol.* 10, 291-297.
13. Velagapudi, S. P., Cameron, M. D., Haga, C. L., Rosenberg, L. H., Lafitte, M., Duckett, D. R., Phinney, D. G., and Disney, M. D. (2016) Design of a small molecule against an oncogenic noncoding RNA. *Proc. Natl. Acad. Sci. U S. A.* 113, 5898-5903.
14. Sugiyama, H., Kilkuskie, R. E., Chang, L. H., Ma, L. T., Hecht, S. M., Vandermarel, G. A., and Vanboom, J. H. (1986) DNA strand scission by bleomycin-catalytic cleavage and strand selectivity. *J. Am. Chem. Soc.* 108, 3852-3854.
15. Sugiyama, H., Kilkuskie, R. E., Hecht, S. M., Vandermarel, G. A., and Vanboom, J. H. (1985) An efficient, site-specific DNA target for bleomycin. *J. Am. Chem. Soc.* 107, 7765-7767.
16. Carter, B. J., de Vroom, E., Long, E. C., van der Marel, G. A., van Boom, J. H., and Hecht, S. M. (1990) Site-specific cleavage of RNA by Fe(II).bleomycin. *Proc. Natl. Acad. Sci. U S. A.* 87, 9373-9377.
17. Abraham, A. T., Lin, J. J., Newton, D. L., Rybak, S., and Hecht, S. M. (2003) RNA cleavage and inhibition of protein synthesis by bleomycin. *Chem. Biol.* 10, 45-52.
18. Burger, R. M. (1998) Cleavage of Nucleic Acids by Bleomycin. *Chem. Rev.* 98, 1153-1170.
19. Hecht, S. M. (1986) The chemistry of activated bleomycin. *Acc. Chem. Res.* 19, 383-391.
20. Kane, S. A., and Hecht, S. M. (1994) Polynucleotide recognition and degradation by bleomycin. *Prog. Nucleic Acid Res. Mol. Biol.* 49, 313-352.
21. Stubbe, J., and Kozarich, J. W. (1987) Mechanisms of bleomycin-induced DNA degradation. *Chem. Revi.* 87, 1107-1136.
22. Berry, D. E., Chang, L. H., and Hecht, S. M. (1985) DNA damage and growth inhibition in cultured human cells by bleomycin congeners. *Biochemistry* 24, 3207-3214.
23. Boger, D. L., Colletti, S. L., Honda, T., and Menezes, R. F. (1994) Total synthesis of Bleomycin A2 and related agents. 1. Synthesis and DNA binding properties of the extended C-terminus: tripeptide S, tetrapeptide S, pentapeptide S, and related agents. *J. Am. Chem. Soc.* 116, 5607-5618.
24. Boger, D. L., Colletti, S. L., Teramoto, S., Ramsey, T. M., and Zhou, J. (1995) Synthesis of key analogs of bleomycin A2 that permit a systematic evaluation of the linker region: identification of an exceptionally prominent role for the L-threonine substituent. *Bioorg. Med. Chem.* 3, 1281-1295.
25. Boger, D. L., Ramsey, T. M., Cai, H., Hoehn, S. T., and Stubbe, J. (1998) Definition of the effect and role of the Bleomycin A2 valerate substituents: preorganization of a rigid, compact conformation implicated in sequence-selective DNA cleavage. *J. Am. Chem. Soc.* 120, 9149-9158.
26. Otsuka, M., Masuda, T., Haupt, A., Ohno, M., Shiraki, T., Sugiura, Y., and Maeda, K. (1990) Synthetic studies on antitumor antibiotic, bleomycin. 27. Man-designed bleomycin with altered sequence specificity in DNA cleavage. *J. Am. Chem. Soc.* 112, 838-845.
27. Owa, T., Haupt, A., Otsuka, M., Kobayashi, S., Tomioka, N., Itai, A., Ohno, M., Shiraki, T., Uesugi, M., Sugiura, Y., and Maeda, K. (1992) Man-designed bleomycins: significance of the binding sites as enzyme models and of the stereochemistry of the linker moiety. *Tetrahedron* 48, 1193-1208.
28. Ma, Q., Xu, Z., Schroeder, B. R., Sun, W., Wei, F., Hashimoto, S., Konishi, K., Leitheiser, C. J., and Hecht, S. M. (2007) Biochemical evaluation of a 108-member deglycobleomycin library: viability of a selection strategy for identifying bleomycin analogues with altered properties. *J. Am. Chem. Soc.* 129, 12439-12452.
29. Thomas, C. J., Chizhov, A. O., Leitheiser, C. J., Rishel, M. J., Konishi, K., Tao, Z. F., and Hecht, S. M. (2002) Solid-phase synthesis of bleomycin A(5) and three monosaccharide analogues: exploring the role of the carbohydrate moiety in RNA cleavage. *J. Am. Chem. Soc.* 124, 12926-12927.
30. Xu, Z. D., Wang, M., Xiao, S. L., Liu, C. L., and Yang, M. (2003) Synthesis, biological evaluation and DNA binding properties of novel bleomycin analogues. *Bioorg. Med. Chem. Lett.* 13, 2595-2599.
31. Rzuczek, S. G., Colgan, L. A., Nakai, Y., Cameron, M. D., Furling, D., Yasuda, R., and Disney, M. D. (2017) Precise small-molecule recognition of a toxic CUG RNA repeat expansion. *Nat. Chem. Biol.* 13, 188-193.
32. Guttilla, I. K., and White, B. A. (2009) Coordinate regulation of FOXO1 by miR-27a, miR-96, and miR-182 in breast cancer cells. *J. Biol. Chem.* 284, 23204-23216.
33. Angelbello, A. J., and Disney, M. D. (2018) Bleomycin can cleave an oncogenic noncoding RNA. *Chembiochem* 19, 43-47.
34. Moon, M. H., Hilimire, T. A., Sanders, A. M., and Schneekloth, J. S., Jr. (2018) Measuring RNA-Ligand Interactions with Microscale Thermophoresis. *Biochemistry* 57, 4638-4643.
35. Jerabek-Willemsen, M., Wienken, C. J., Braun, D., Baaske, P., and Duhr, S. (2011) Molecular interaction studies using microscale thermophoresis. *Assay Drug Dev. Technol.* 9, 342-353.
36. Lane, S. I. R., Morgan, S. L., Wu, T., Collins, J. K., Merriman, J. A., ElInati, E., Turner, J. M., and Jones, K. T. (2017) DNA damage induces a kinetochore-based ATM/ATR-independent SAC arrest unique to the first meiotic division in mouse oocytes. *Development* 144, 3475-3486.
37. Esquela-Kerscher, A., and Slack, F. J. (2006) Oncomirs-microRNAs with a role in cancer. *Nat. Rev. Cancer* 6, 259-269.
38. Agarwal, V., Bell, G. W., Nam, J. W., and Bartel, D. P. (2015) Predicting effective microRNA target sites in mammalian mRNAs. *Elife* 4, e05005.
39. Stern, S., Moazed, D., and Noller, H. F. (1988) Structural analysis of RNA using chemical and enzymatic probing monitored by primer extension. *Methods Enzymol.* 164, 481-489.
40. Moazed, D., and Noller, H. F. (1987) Interaction of antibiotics with functional sites in 16S ribosomal-RNA. *Nature* 327, 389-394.
41. Kwok, C. K., Ding, Y., Tang, Y., Assmann, S. M., and Bevilacqua, P. C. (2013) Determination of in vivo RNA structure in low-abundance transcripts. *Nat. Commun.* 4, 2971.
42. Guan, L., and Disney, M. D. (2013) Small-molecule-mediated cleavage of RNA in living cells. *Angew. Chem. Int. Ed. Engl.* 52, 1462-1465.
43. Nguyen, L., Luu, L. M., Peng, S., Serrano, J. F., Chan, H. Y., and Zimmerman, S. C. (2015) Rationally designed small molecules that target both the DNA and RNA causing myotonic dystrophy type 1. *J. Am. Chem. Soc.* 137, 14180-14189.
44. Costales, M. G., Matsumoto, Y., Velagapudi, S. P., and Disney, M. D. (2018) Small molecule targeted recruitment of a nuclease to RNA. *J. Am. Chem. Soc.* 140, 6741-6744.
45. Gu, S., Cui, D., Chen, X., Xiong, X., and Zhao, Y. (2018) PROTACs: an emerging targeting technique for protein degradation in drug discovery. *Bioessays* 40, e1700247.

TABLE 1

Sequences of primers used in this study.

| Primer | Sequence (5' to 3') |
|---|---|
| miR-96 | TTTGGCACTAGCACATTTTTGCT (SEQ. ID NO: 1) |
| pri-miRNA-96-F | AGAGAGCCCGCACCAGT (SEQ. ID NO: 2) |
| pri-miRNA-96-R | CTTGAGGAGGAGCAGGCT (SEQ. ID NO: 3) |
| RNU6 | ACACGCAAATTCGTGAAGCGTTC (SEQ. ID NO: 4) |
| Universal reverse | GAATCGAGCACCAGTTACGC (SEQ. ID NO: 5) |
| miR-10b | TACCCTGTAGAACCGAATTTGTG (SEQ. ID NO: 6) |
| miR-21 | TAGCTTATCAGACTGATGTTGA (SEQ. ID NO: 7) |
| miR-27a | TTCACAGTGGCTAAGTTCCGC (SEQ. ID NO: 8) |
| miR-9 | TCTTTGGTTATCTAGCTGTATGA (SEQ. ID NO: 9) |
| miR-194 | TGTAACAGCAACTCCATGTGGA (SEQ. ID NO: 10) |
| miR-15a | TAGCAGCACATAATGGTTTGTG (SEQ. ID NO: 11) |
| miR-16 | TAGCAGCACGTAAATATTGGCG (SEQ. ID NO: 12) |
| miR-139 | TCTACAGTGCACGTGTCTCCAGT (SEQ. ID NO: 13) |
| miR-182 | TTTGGCAATGGTAGAACTCACACT (SEQ. ID NO: 14) |
| miR-196a | TAGGTAGTTTCATGTTGTTGGG (SEQ. ID NO: 15) |

TABLE 1-continued

| Sequences of primers used in this study. | |
|---|---|
| Primer | Sequence (5' to 3') |
| miR-128a | TCACAGTGAACCGGTCTCTTT (SEQ. ID NO: 16) |
| miR-142 | TGTAGTGTTTCCTACTTTATGGA (SEQ. ID NO: 17) |
| miR-223 | TGTCAGTTTGTCAAATACCCC (SEQ. ID NO: 18) |
| miR-101 | TACAGTACTGTGATAACTGAA (SEQ. ID NO: 19) |
| miR-132 | TAACAGTCTACAGCCATGGTCG (SEQ. ID NO: 20) |
| miR-212 | TAACAGTCTCCAGTCACGGCC (SEQ. ID NO: 21) |
| miR-135a | TATGGCTTTTTATTCCTATGTGA (SEQ. ID NO: 22) |
| miR-1271 | CTTGGCACCTAGCAAGCACTCA (SEQ. ID NO: 23) |

EXAMPLES

Experimental Procedures

RNA preparation: The single-stranded DNA template (5'-GGGTGGCCGATTTTGGCACTAGCACAT-TTTTGCTTGTGTCTCTCCGCTCTGAGCAA TCATGTGCAGTGCCAATATGGGAAA-3') (SEQ. ID NO:24) for PCR amplification was purchased from Integrated DNA Technologies, Inc. (IDT) and used without further purification. PCR amplification was performed in 1×PCR Buffer (10 mM Tris, pH 9.0, 50 mM KCl, and 0.1% (v/v) Triton X-100), 2 μM T7 promoter forward primer (5'-GGCCGGATCCTAATACGACTCAC-TATAGGGTGGCCGATTTTGGC-3') (SEQ. ID NO:25), 2 μM reverse primer (5'-TTTCCCATATTGGCA-3') (SEQ. ID NO:26), 4.25 mM $MgCl_2$, 330 μM dNTPs, and 1 μL of Taq DNA polymerase in a 300 μL reaction. The cycling conditions used for PCR were 95° C. for 30 s, 55° C. for 30 s, and 72° C. for 1 min. The resulting double stranded DNA template was transcribed by T7 RNA polymerase in 1× Transcription Buffer (40 mM Tris HCl, pH 8.1, 1 mM spermidine, 0.001% (v/v) Triton X-100 and 10 mM DTT) containing 2.25 mM of each rNTP and 5 mM $MgCl_2$ at 37° C. overnight. The RNA product was purified on a denaturing 15% polyacrylamide gel, and concentrations were determined by UV absorbance at 260 nm.

In vitro RNA cleavage and primer extension: The pri-miR-96 RNA (1 μM) was folded as previously described[2] by heating at 65° C. for 5 min and slowly cooling to room temperature. Different concentrations of 2 or 3 (5, 50, 500 nM) were pre-activated by the addition of 1 eq $Fe^{2+}$ and added to the folded RNA in a total volume of 20 μL. Next, 1 eq $Fe^{2+}$ was added 30 min and then 60 min later, and the reaction mixtures were incubated at 37° C. overnight.[3] After ethanol precipitation and quantification by Nanodrop, reverse transcription was performed by using SuperScript™ III Reverse Transcriptase (ThermoFisher Scientific) per the manufacturer's protocol using 5' $^{32}P$-labeled primer (~10,000 counts). The A, T, G and C sequencing ladders were generated by using a ratio of ddNTP/dNTP of 3:1. The RNA was digested by the addition of RNase A and RNase H and incubated at 37° C. for 30 min. Then, an equal volume of Loading Buffer (95% formaldehyde, 50 mM EDTA, 0.05% (w/v) bromophenol blue, 0.05% (w/v) xylene cyanol) was added to each reaction. The final mixture was resolved on a denaturing 15% polyacrylamide gel.

DNA cleavage in vitro: Different concentrations of 2 or 3 (5, 50, 500, 5000 and 10000 nM) were pre-activated by the addition of 1 eq $Fe^{2+}$ and then 2 μL of a plasmid encoding GFP (150 ng/μL) was added in a final volume of 20 μL. An additional equivalent of $Fe^{2+}$ was added 30 min and then 60 min later, and the reaction mixture was incubated at 37° C. overnight. The reaction mixture was loaded on 0.8% agarose gel with 6×Gel Loading Dye, Purple (NEB) and stained with ethidium bromide for 10 min.

Visualization of DNA damage: MDA-MB-231 cells were grown in a glass bottom 96-well plate and treated with compound for 24 h. Cells were washed with 1×DPBS three times and then fixed with 100 μL of 4% paraformaldehyde for 10 min at 37° C. Cells were washed with 1×DPBS three times and then with 0.1% Triton X-100 in 1×DPBS three times for 5 min at 37° C. Cells were then incubated with a 1:500 dilution of anti-γH2AX (Abcam)[4] at 37° C. for 1 h, washed three times with 0.1% Triton X-100 in 1×DPBS for 5 min at 37° C., and incubated with a 1:200 dilution of goat anti-mouse IgG-DyLight 488 conjugate (Thermo Scientific) at 37° C. for 1 h. After washing the cells with 0.1% Triton in 1×DPBS and twice with 1×DPBS for 5 min at 37° C., nuclei were stained with DAPI (100 μL of 1 μg/mL), and cells were imaged.

RT-qPCR of miRNAs: Cells (~70% confluency) were treated with various concentrations of compound for 24 h. Total RNA was extracted using a Quick-RNA Miniprep Kit (Zymo Research) per the manufacturer's protocol. Approximately 200 ng of total RNA, as determined by Nanodrop, was used for reverse transcription using a miScript II RT Kit (Qiagen) per the manufacturer's protocol. RT-qPCR was performed on a 7900HT Fast Real Time PCR System (Applied Biosystem) using Power SYBR Green Master Mix (Applied Biosystems). All primers were purchased from IDT and listed in Table 51. The primers for unbiased miRNA profiling were purchased from Eurofins Genomics in a 384-well plate. The expression levels of miRNAs were normalized to U6 small nuclear RNA.[5]

Western blotting: Cells in 6-well plates (~70% confluency) were treated with 500 nM of 2 for 48 h. Total protein was extracted using M-PER Mammalian Protein Extraction Reagent (Pierce Biotechnology) following the manufacturer's protocol and quantified using a Micro BCA Protein Assay Kit (Pierce Biotechnology). Approximately 20 μg total protein was separated on a 10% SDS-polyacrylamide gel, and then transferred to a PVDF membrane. The membrane was washed with 1×Tris-buffered saline (TBS) and then blocked in 5% milk in 1×TBST (1×TBS containing 0.1% Tween-20) for 1 h at room temperature. After incubation in 1:1000 FOXO1 primary antibody (Cell Signaling Technology) in 1×TBST containing 5% milk overnight at 4° C., the membrane was washed with 1×TBST and incubated with 1:2000 anti-rabbit IgG horseradish-peroxidase secondary antibody conjugate (Cell Signaling Technology) in 1×TBS for 1 h at room temperature. The membrane was washed with 1×TBST and protein expression was quantified using SuperSignal West Pico Chemiluminescent Substrate (Pierce Biotechnology) per the manufacturer's protocol. To quantify β-actin expression, the membrane was stripped using 1× Stripping Buffer (200 mM glycine, pH 2.2 and 0.1% SDS) followed by washing in 1×TBST. The membrane was blocked and probed for β-actin similarly using 1:5000β-actin primary antibody (Cell Signaling Technology) in 1×TBST containing 5% milk at room temperature for 1 h. The membrane was washed with 1×TBST and incubated with 1:10,000 antirabbit IgG horseradish-peroxidase secondary antibody conjugate (Cell Signaling Technology) in 1×TBS for 1 h at room temperature. β-actin protein expression was quantified using SuperSignal West Pico Chemiluminescent Substrate (Pierce Biotechnology) per the manufacturer's protocol. The fold change of FOXO1 expression was calculated by normalizing FOXO1 band intensity to β-actin band intensity.

Caspase assay: Cells in 96-well plates (~60% confluency) were treated with various concentrations of compound for 48 h. In the case of miR-96 overexpression, cells were transfected with a plasmid encoding pri-miR-96 with Lipofectamine 2000 (Thermo Fisher Scientific) per the manufacturer's protocol, split into 96-well plates, and treated with compounds for 48 h. MCF 10A cells were cultured in Dulbecco's modified eagle medium/F12 (DMEM/F12) supplemented with 20 ng/μL epidermal growth factor (EGF), 0.5 μg/mL hydrocortisone, cholera toxin 0.1 μg/mL, bovine insulin 10 μg/mL, 1% penicillin/streptomycin and 10% FBS (complete growth medium).Caspase-3/7 activities were measured by using Caspase-Glo® 3/7 Assay Systems (Promega) per the manufacturer's protocol. Luminescence of compound-treated wells was normalized to untreated cells, and the fold change of caspase activities was calculated.

Annexin V/PI Assay: Cells in 6-well plates (~60% confluency) were incubated with 2 or 3 for 48 h. As a positive control, cells were treated with 10 μM camptothecin for 24 h. The cells were detached from the surface by using accutase and washed twice with ice-cold 1×DPBS and then three times with 1×Annexin Binding Buffer (50 mM Hepes (pH 7.4), 700 mM NaCl and 12.5 mM $CaCl_2$)). The cells were suspended in 100 μL 1×Annexin Binding Buffer containing 5 μL Annexin V-APC (eBioscience). The cells were incubated for 10 min at room temperature followed by washing with 1×Annexin Binding Buffer. The cells were then stained with 1 μg/mL propidium iodide in 300 μL of 1×Annexin Binding Buffer for 15 min at room temperature. Flow cytometry was performed using a BD LSRII instrument (BD Biosciences). For data analysis, the appropriate quadrant was assigned, and the early and late apoptosis percentages, as shown by Annexin V and PI staining, were calculated.

Molecular modeling: Modeling of the binding of 2 to pri-miR-96 was generated as previously reported[6]. Briefly, we first modeled the binding of 1 to pri-miR-96. The target RNA structure was modeled in RNAComposer (http://macomposer.cs.put.poznan.pl/) using the secondary structure predicted with ViennaRNA (http://ma.tbi.univie.ac.at/). The RNA-binding small molecule was energy minimized using MacroModel (Schrodinger, LLC, NY) and placed proximal to the RNA. Energy minimization of the RNA-small molecule complex was performed until the gradient of energy was less than 0.01 kcal/mol/A. The bleomycin A5 moiety was then manually added and allowed flexibility during an additional energy minimization to model the binding of 2 to pri-miR-96. Energy minimization was performed until the gradient of energy was less than 0.01 kcal/mol/A. The conformation with lowest energy is shown in Figure S8.

Ribo-SNAP-Map[7-8]: Cells were grown in 100 mm dishes to ~70% confluency and treated with 1 (control), 2, or 3 (control) for 6 h. Total RNA was then extracted by treatment with TRIzol (ThermoFisher Scientific) and quantified by Nanodrop. Approximately 10 μg of total RNA was used for reverse transcription with a pri-miR-96 specific primer (5'-CAGACGTGTGCTCTTCC-GATCTCGCAGCTGCGGGTCCT-3'; (SEQ. ID NO:27) 2 pmol) using Superscript III (SSIII; Life Technologies). 10 μg RNA with 2 pmol of gene-specific primer and 1 μL 10 mM dNTP Mix in total 13 μL was kept at 65° C. for 5 min and in ice for 5 min. Then 4 μL 5× First-Strand Buffer, 1 μL 0.1 M DTT, 1 μL RNaseOUT and 1 μL SuperScript™ III RT were added and incubated at 50° C. for 1 h and then 85° C. for 10 min. After digesting the RNA with RNase A and RNase H, the cDNA was purified by using RNAClean XP beads (Beckman Coulter; 1.8 volumes of beads and 3 volumes of isopropanol).

The purified cDNA was ligated with a 3' adapter (/5Phos/AGATCGGAAGAGCGTCGTGTAG/3Bio/)(SEQ. ID NO:28) by T4 RNA ligase 1 (New England BioLabs; NEB) following the manufacturer's recommended protocol (2 μL 10×T4 RNA ligase buffer, 1 μL of 1 mM ATP, 10 μL 50% PEG 8000, 5 μL cDNA, 1 μL of 20 μM ssDNA adaptor, and 1 μL of T4 RNA ligase). Then, the cDNA ligated to the adaptor was purified with RNAClean XP beads as described above. PCR amplification was performed with the ligated cDNA by using Phusion polymerase (NEB) with cycles of 98° C. for 20 s, 64° C. for 20 s and 72° C. for 90 s and the following primers: forward-(5'-CA-GACGTGTGCTCTTCCGATC-3') (SEQ. ID NO:29); reverse-(5'-CTACACGACGCTCTTCCGATCT-3') (SEQ. ID NO:30). The PCR products were then 5'-end labeled with $^{32}P$ as described above and separated on a denaturing 15% polyacrylamide gel. A 100 bp ladder (NEB) was used as a marker. For Sanger sequencing, the PCR products were separated on a denaturing 15% polyacrylamide gel, and the target band was excised from gel and ethanol precipitated. The purified DNA was ligated into a vector by using NEB's PCR Cloning Kit per the manufacturer's protocol. Antibiotic-resistant colonies were selected and subjected to Sanger sequencing by Genewiz.

Scheme 1. Synthetic route for 2 and 3

Scheme 1

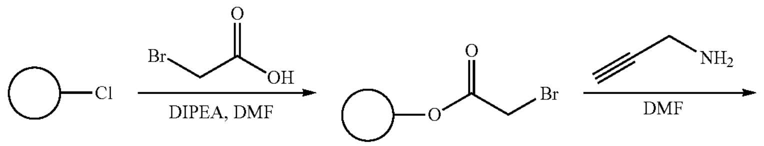

-continued
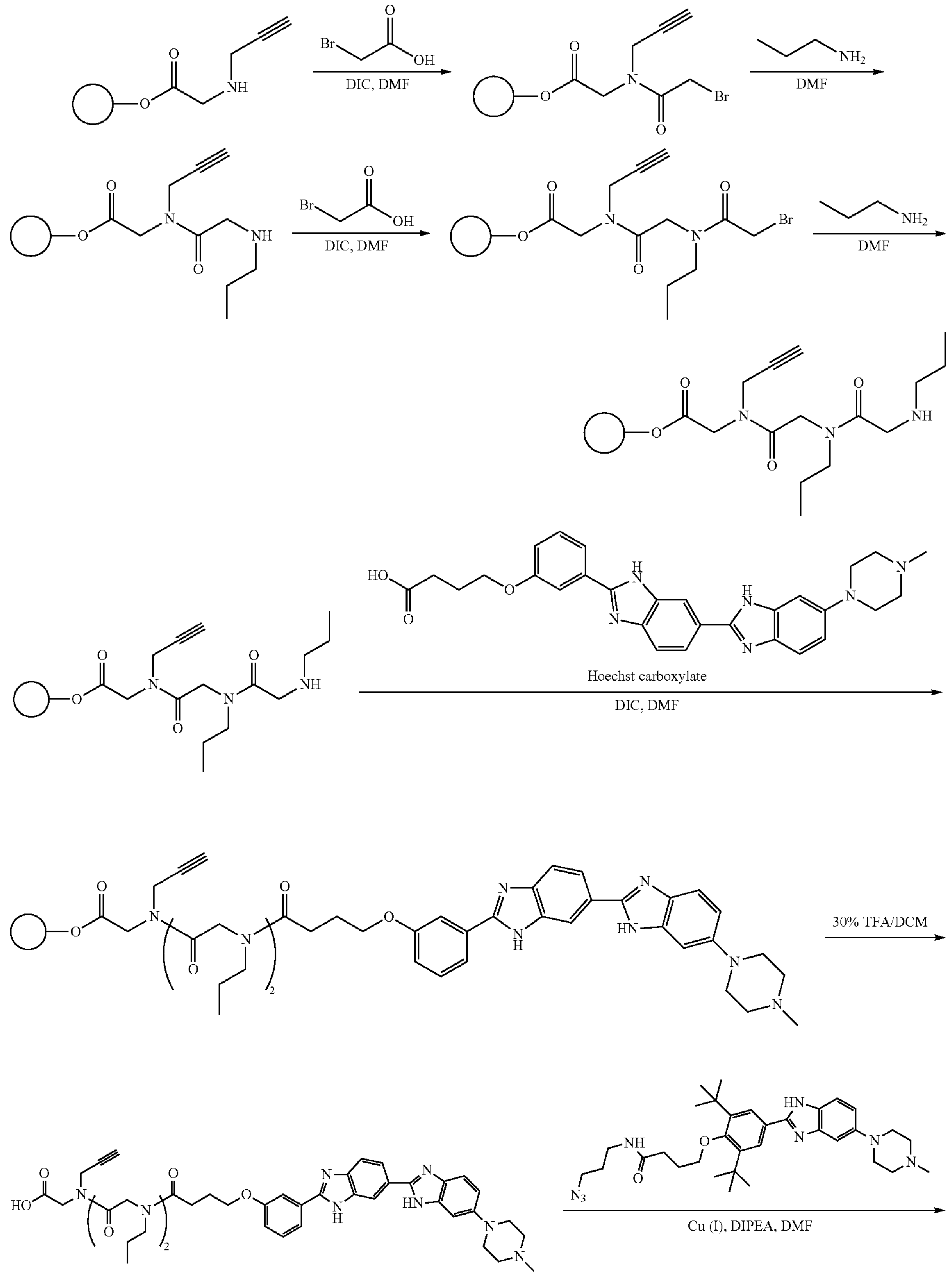

-continued
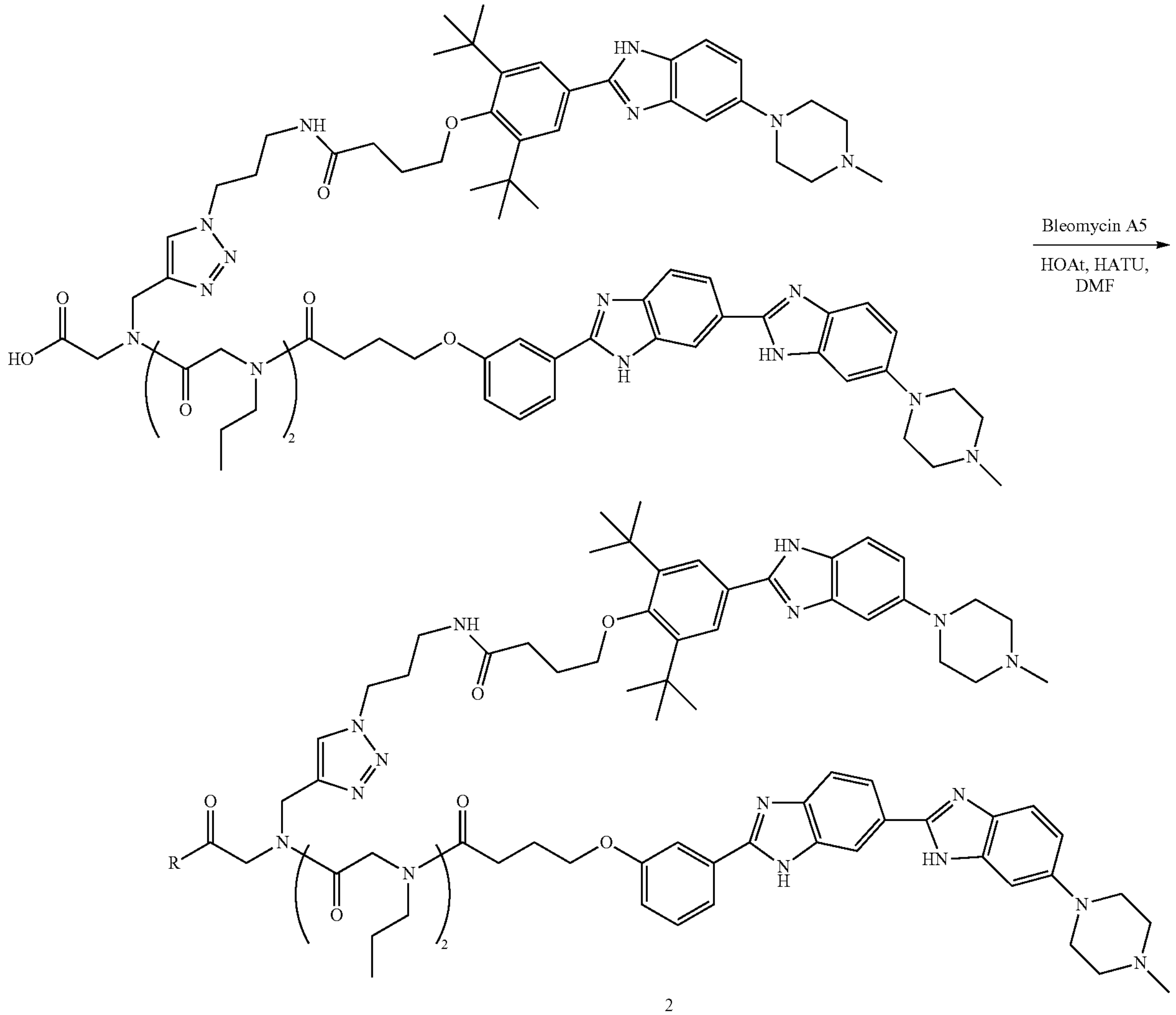
2
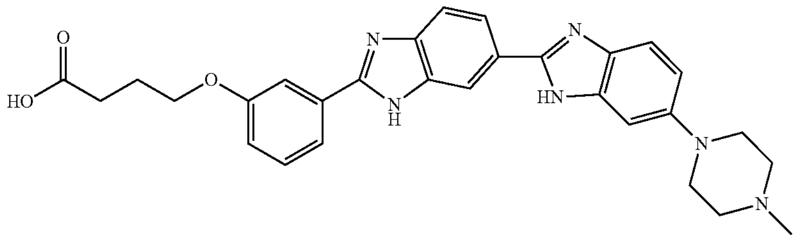
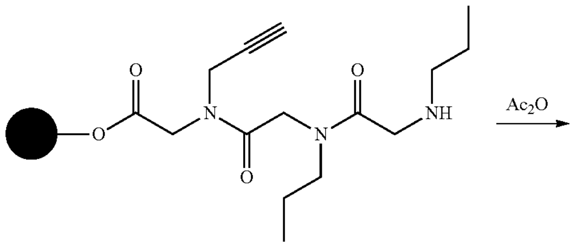

-continued

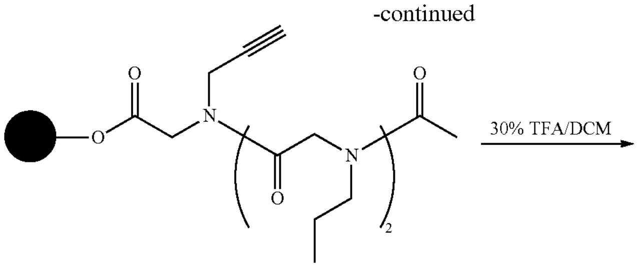

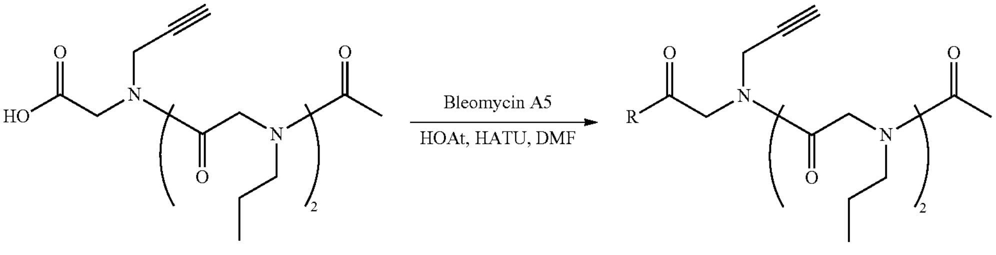

3

R =

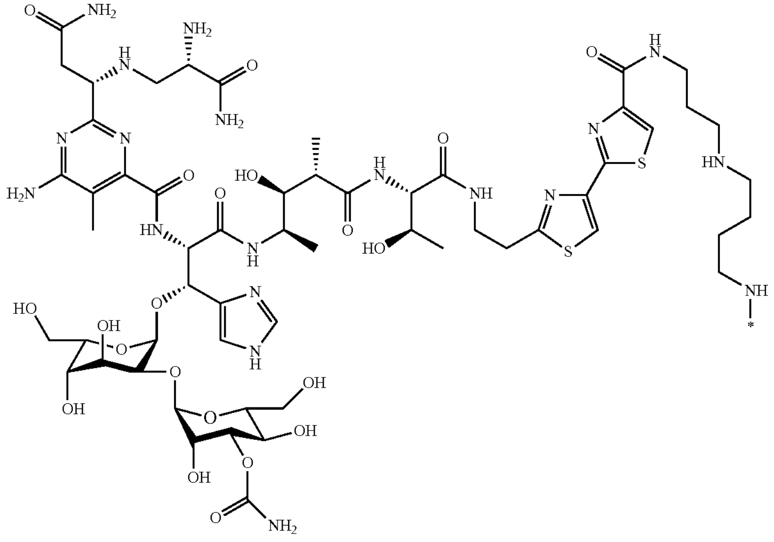

Synthesis of compound 1: Compound 1 was synthesized as previously described.[5] Briefly, Rink amide resin (500 mg, 345 μmol) with a substitution level of 0.69 mmol/g was shaken in N,N-dimethyl formamide (DMF) for 5 min and then deprotected with 20% piperidine in DMF (10 mL, 2×30 min) at room temperature. The resin was washed with 10 mL DMF three times. Next, 5 eq of bromoacetic acid in 10 mL DMF solution and 5 eq of DIC (N,N'-diisopropylcarbodiimide) were added, and the resin was shaken at room temperature for 30 min. After washing with 10 mL DMF three times, 5 eq of propargylamine in 10 mL DMF was added, and the reaction mixture was shaken at room temperature for 2 h. The bromoacetic acid coupling step was repeated and 5 eq propylamine in 10 mL DMF was added, and the reaction mixture was shaken at room temperature for 2 h. The bromoacetic acid coupling step and propylamine step were repeated. The peptoid in the resin was then treated with a solution of 2 eq Hoechst carboxylate (synthesized as previously described)[9], 2 eq DIC and 2 eq DIPEA (N,N'-diisopropylethylamine) in 10 mL DMF. The reaction mixture was shaken at room temperature for 2 h and washed with 10 mL DMF three and then 10 mL dichloromethane (DCM) three times. The product was cleavage from resin by adding 10 mL 30% trifluoroacetic acid (TFA) in DCM and shaken 30 min at room temperature. The eluate was concentrated under vacuum, and the product was precipitated with excess amounts of ether.

The resulting yellow solid was directly treated with a solution of 1.1 eq azide[2], 0.2 eq Cu(I) catalyst and 2 eq DIEA in 2 mL DMF. The reaction mixture was kept at 65° C. overnight, and the reaction process was monitored by MALDI-TOF MS. After the starting material was no longer detectable, the product was precipitated with excess amounts of ether and dissolved in 50% methanol in water with 0.1% TFA. HPLC purification was performed with a linear gradient from 0% to 100% B (methanol or acetonitrile+0.1% TFA) in A (water+0.1% TFA) over 60 min and a flow rate of 5 mL/min. The pure fractions were collected, and the solvent was concentrated under vacuum. Excess amounts of ether were added, and the resulting solid was obtained as product. Purity was evaluated on a reverse phase Waters Symmetry C18 5 μm 4.6×150 mm column at room temperature with a flow rate of 1 mL/min and a linear gradient of 0-100% B in A. Absorbance was monitored at 254 nm and 345 nm. Mass spectra were recorded on a 4800 plus MALDI-TOF/TOF analyzer. MALDI: $[M+H]^+$ calculated: 1391.8179; $[M+H]^+$ observed: 1391.9153.

Synthesis of compound 2: Chlorotrityl resin (500 mg, 580 μmol) was activated in 1 M HCl in 10 mL DCM for 10 min at room temperature, followed by washing with DCM three times and DMF three times. Next, 5 eq of bromoacetic acid and 5 eq DIPEA in 10 mL DMF were added, and the resin shaken at room temperature for 30 min. After washing with 10 mL DMF three times, 5 eq propargylamine in 10 mL DMF were added, and the reaction mixture was shaken at room temperature for 2 h. The resin was washed with 10 mL DMF three times and 5 eq of bromoacetic acid in 10 mL DMF solution and 5 eq DIC were added. The resin was shaken at room temperature for 30 min followed by addition of 5 eq propylamine in 10 mL DMF. The reaction mixture was shaken at room temperature for 2 h. The bromoacetic acid coupling step and propylamine step were repeated. The peptoid on the resin was then treated with a solution of 2 eq Hoechst carboxylate, 2 eq DIC and 2 eq DIPEA in 10 mL DMF solution. The reaction mixture was shaken at room temperature for 2 h and washed with 10 mL DMF three times and then 10 mL DCM three times. The product was cleaved from resin by adding 10 mL of 30% TFA in DCM and shaking the resin for 30 min at room temperature. The elutate was concentrated under vacuum, and the product was precipitated with an excess amount of ether.

The resulting solid was directly treated with a solution of 1.1 eq azide, 0.2 eq Cu(I) catalyst and 2 eq DIEA in 2 mL DMF. The reaction mixture was kept 65° C. overnight, and the reaction process was monitored by MALDI MS. After the starting material was no longer detectable, the product was precipitated with an excess amount of ether.

The Bleomycin A5 coupling reaction was performed by adding 2 eq HOAt (1-Hydroxy-7-azabenzotriazole), 2 eq HATU (hexafluorophosphate azabenzotriazole tetramethyl uronium), 5 eq DIEA, and 2 eq Copper-bleomycin A5. The reaction mixture was shaken at room temperature overnight and the product was precipitated with an excess amount of ether. The solid was dissolved in 50% acetonitrile in water with 0.1% TFA and subjected to HPLC purification. After injection of the solution, the column was washed with 50 mM EDTA (pH 6.7) for 30 min to remove the copper ion and then washed with water for another 30 min. Then the target product was separated with a linear gradient from 0% to 100% B (acetonitrile+0.1% TFA) in A (water+0.1% TFA) over 60 min and a flow rate of 5 mL/min. The pure product was obtained and characterized as described above. MALDI: $[M+H]^+$ calculated: 1775.7767; $[M+H]^+$ observed: 1775.4158.

Synthesis of compound 3: Chlorotrityl resin (500 mg, 580 μmol) was activated in 1 M HCl in 10 mL DCM for 10 min at room temperature, followed by washing with DCM three times and DMF three times. Then, 5 eq bromoacetic acid and 5 eq DIPEA in 10 mL of DM were added, and the resin was shaken at room temperature for 30 min. After washing with 10 mL DMF three times, 5 eq propargylamine in 10 mL DMF was added, and the reaction mixture was shaken at room temperature for 2 h. The resin was washed with 10 mL DMF three times followed by addition of 5 eq of bromoacetic acid in 10 mL DMF solution and 5 eq DIC. The resin was shaken at room temperature for 30 min and then 5 eq propylamine in 10 mL DMF were added. After shaking the mixture at room temperature for 2 h, the bromoacetic acid coupling step and propylamine step were repeated. The peptoid on the resin was then treated with a solution of 2 eq acetic anhydride ($Ac_2O$) and 2 eq DIPEA in 10 mL DMF. The reaction mixture was shaken at room temperature for 30 min and washed with 10 mL DMF three times and then 10 mL DCM three times. The product was cleaved from the resin by adding 10 mL 30% TFA in DCM and shaking at room temperature for 30 min. The eluate was concentrated under vacuum, and the product was precipitated with excess amount of ether.

The Bleomycin A5 coupling reaction was performed by adding 2 eq HOAt, 2 eq HATU, 5 eq DIEA and 2 eq Copper-Bleomycin A5. The reaction mixture was shaken at room temperature overnight, and the product was precipitated with an excess amount of ether. The solid was dissolved in 50% acetonitrile in water with 0.1% TFA and subjected to HPLC purification. After injection of the solution, the column was washed with 50 mM EDTA (pH 6.7) for 30 min to remove the copper ion and then washed with water for another 30 min. Then the target product was separated with a linear gradient from 0% to 100% B (acetonitrile+0.1% TFA) in A (water+0.1% TFA) over 60 min and a flow rate of 5 mL/min. The pure product was obtained and characterized as described above. MALDI: $[M+H]^+$ calculated: 1928.7767; $[M+H]^+$ observed: 1928.8219.

DOCUMENTS CITED IN EXAMPLES SECTION

1. Jerabek-Willemsen, M., Wienken, C. J., Braun, D., Baaske, P., and Duhr, S. (2011) Molecular interaction studies using microscale thermophoresis. *Assay Drug De. v Technol.* 9, 342-353.
2. Agarwal, V., Bell, G. W., Nam, J. W., and Bartel, D. P. (2015) Predicting effective microRNA target sites in mammalian mRNAs. *Elife* 4, e05005.
3. Velagapudi, S. P., Gallo, S. M., and Disney, M. D. (2014) Sequence-based design of bioactive small molecules that target precursor microRNAs. *Nat. Chem. Biol.* 10, 291-297.
4. Angelbello, A. J., and Disney, M. D. (2018) Bleomycin can cleave an oncogenic noncoding RNA. *Chembiochem* 19, 43-47.
5. Lane, S. I. R., Morgan, S. L., Wu, T., Collins, J. K., Merriman, J. A., Ellnati, E., Turner, J. M., and Jones, K. T. (2017) DNA damage induces a kinetochore-based ATM/ATR-independent SAC arrest unique to the first meiotic division in mouse oocytes. *Development* 144, 3475-3486.
6. Velagapudi, S. P., Cameron, M. D., Haga, C. L., Rosenberg, L. H., Lafitte, M., Duckett, D. R., Phinney, D. G., and Disney, M. D. (2016) Design of a small molecule against an oncogenic noncoding RNA. *Proc. Natl. Acad. Sci. U.S.A.* 113, 5898-5903.
7. Costales, M. G., Matsumoto, Y., Velagapudi, S. P., and Disney, M. D. (2018) Small molecule targeted recruitment of a nuclease to RNA. *J. Am. Chem. Soc.* 140, 6741-6744.
8. Fang, R., Moss, W. N., Rutenberg-Schoenberg, M., and Simon, M. D. (2015) Probing Xist RNA structure in cells using targeted structure-seq. *PLoS Genet.* 11, e1005668.
9. Sexton, A. N., Wang, P. Y., Rutenberg-Schoenberg, M., and Simon, M. D. (2017) Interpreting reverse transcriptase termination and mutation events for greater insight into the chemical probing of RNA. *Biochemistry* 56, 4713-4721.
10. Pushechnikov, A., Lee, M. M., Childs-Disney, J. L., Sobczak, K., French, J. M., Thornton, C. A., and Disney, M. D. (2009) Rational design of ligands targeting triplet repeating transcripts that cause RNA dominant disease: application to myotonic muscular dystrophy type 1 and spinocerebellar ataxia type 3. *J. Am. Chem. Soc.* 131, 9767-9779.

All patents and publications referred to herein are incorporated by reference herein to the same extent as if each individual publication was specifically and individually indicated to be incorporated by reference in its entirety.

What is claimed is:

1. A method comprising contacting a library of RNA sequences and an effective amount of a compound comprising a conjugate of an RNA-cleaving moiety and an RNA-binding small molecule to cleave the RNA of the library at a binding site of the compound to the RNA to provide a cleaved RNA fragment;

amplifying and sequencing the cleaved RNA fragment, thereby identifying the site of binding of the small RNA-binding molecule to the RNA of the library which is associated with the site of cleavage; and wherein at least one of the RNA sequences is from an oncogenic non-coding RNA precursor, and the compound binds to the oncogenic non-coding RNA precursor.

2. The method of claim 1, wherein the RNA-binding small molecule comprises an N-methyl-piperazinyl-bis-benzimidazole group.

3. The method of claim 1, wherein the RNA-cleaving moiety comprises bleomycin.

4. The method of claim 3, wherein the bleomycin is bleomycin A5.

5. The method of claim 2, wherein the RNA-binding small molecule is Targaprimir-96.

6. The method of claim 1, further comprising contacting a cell expressing the non-coding RNA precursor with an effective amount of the compound.

7. The method of claim 1, wherein the oncogenic non-coding RNA precursor comprises oncogenic primary microRNA-96.

8. The method of claim 1, wherein the compound is a covalent conjugate of Targaprimir-96 and bleomycin A5.

9. The method of claim 1, wherein at least one of the RNA sequences is from FOXO1.

10. The method of claim 9, further comprising enhancing expression of FOXO1 protein in breast cancer cells by contacting the cells with an effective amount of the compound.

11. The method of claim 10, wherein the contacting comprises administering to a human patient.

12. The method of claim 9, wherein the compound is a covalent conjugate of Targaprimir-96 and bleomycin A5.

13. A method of triggering apoptosis in triple negative breast cancer cells, comprising contacting the triple negative breast cancer cells with an effective amount of a compound comprising a conjugate of an RNA-cleaving moiety and an RNA-binding small molecule, wherein the RNA-binding small molecule comprises an N-methyl-piperazinyl-bis-benzimidazole group, and the RNA-cleaving moiety comprises bleomycin.

14. The method of claim 13, wherein the contacting comprises administering to a human patient.

15. The method of claim 13, wherein the compound is a covalent conjugate of Targaprimir-96 and bleomycin A5.

16. A method of treating triple negative breast cancer, comprising administering to a patient afflicted therewith an effective dose of a compound comprising a conjugate of an RNA-cleaving moiety and an RNA-binding small molecule, wherein the RNA-binding small molecule comprises an N-methyl-piperazinyl-bis-benzimidazole group, and the RNA-cleaving moiety comprises bleomycin.

17. The method of claim 16, wherein the breast cancer comprises expression of oncogenic primary microRNA-96.

18. The method of claim 16, wherein the compound is a covalent conjugate of Targaprimir-96 and bleomycin A5.

19. The method of claim 1, wherein the RNA sequence library comprises a transcriptome.

20. The method of claim 19, wherein the transcriptome is viral.

21. The method of claim 1, wherein the RNA sequence library comprises one or more of synthetic, semi-synthetic, or natural RNA.

22. The method of claim 1, wherein the RNA sequence library comprises the genome of an RNA virus.

23. The method of claim 1 carried out in vitro.

24. The method of claim 1 carried out in living cells.

25. The method of claim 24, wherein the cells are virally- or bacterially-infected cells.

26. The method of claim 1, wherein a set of RNA sequences and a set of compounds comprising candidate RNA-binding small molecules are assayed in a 2-dimensional parallel array.

27. A compound comprising a conjugate of an RNA-cleaving moiety and an RNA-binding small molecule, wherein the RNA-binding small molecule is Targaprimir-96.

28. The compound of claim 27, wherein the RNA-cleaving moiety comprises bleomycin.

29. The method of claim 19, wherein the transcriptome is mammalian.

30. The method of claim 19, wherein the transcriptome is bacterial.

31. The method of claim 13, wherein the RNA-binding small molecule is Targaprimir-96.

32. The method of claim 16, wherein the RNA-binding small molecule is Targaprimir-96.

33. A method comprising contacting a library of RNA sequences and an effective amount of a compound comprising a conjugate of an RNA-cleaving moiety and an RNA-binding small molecule to cleave the RNA of the library at a binding site of the compound to the RNA to provide a cleaved RNA fragment;

amplifying and sequencing the cleaved RNA fragment, thereby identifying the site of binding of the small RNA-binding molecule to the RNA of the library which is associated with the site of cleavage; and wherein the RNA-binding small molecule is Targaprimir-96.

* * * * *